United States Patent [19]

Kuehne

[11] Patent Number: 4,841,045
[45] Date of Patent: Jun. 20, 1989

[54] SYNTHESIS OF VINBLASTINE AND VINCRISTINE TYPE COMPOUNDS

[75] Inventor: Martin Kuehne, Burlington, Vt.

[73] Assignee: University of Vermont & State Agricultural College, Burlington, Vt.

[21] Appl. No.: 50,807

[22] Filed: May 18, 1987

Related U.S. Application Data

[63] Continuation-in-part of Ser. No. 810,112, Dec. 18, 1985, abandoned, which is a continuation-in-part of Ser. No. 710,792, Mar. 12, 1985, abandoned.

[51] Int. Cl.$^4$ .................. C07D 519/04; C07D 461/00; C07D 487/04
[52] U.S. Cl. .................................... 540/478; 540/479; 546/51; 546/63; 548/421
[58] Field of Search ..................... 546/51, 63; 540/478, 540/479; 548/421

[56] References Cited

U.S. PATENT DOCUMENTS

| | | | |
|---|---|---|---|
| 2,858,314 | 10/1958 | Georgian | 548/421 X |
| 3,422,112 | 1/1969 | Gorman et al. | 540/478 |
| 4,115,388 | 9/1978 | Thompson et al. | 540/478 |
| 4,122,081 | 10/1978 | Thompson et al. | 540/478 |
| 4,143,041 | 3/1979 | Thompson | 540/478 |
| 4,144,237 | 3/1979 | Kutney | 540/478 |
| 4,279,817 | 7/1981 | Kutney | 540/478 |
| 4,362,739 | 12/1982 | Kuehne | 548/421 X |

FOREIGN PATENT DOCUMENTS

| | | | |
|---|---|---|---|
| 0012674 | 6/1980 | European Pat. Off. | 540/478 |
| 2558124 | 7/1976 | Fed. Rep. of Germany | 540/478 |
| 3518763 | 11/1986 | Fed. Rep. of Germany | |
| WO/86/05491 | 9/1986 | PCT Int'l Appl. | |

OTHER PUBLICATIONS

Kutney et al., J. Am. Chem. Soc., vol. 90, No. 16, pp. 4504–4505 (1968).
Atta-ur-Rahman et al., Z. Naturforsch., 31b, pp. 264–266 (1976).
Kuehne, copy of a lecture given at the Gordon Conference in New Hampton, New Hampshire on Jul. 23, 1985.
Schill, et al., Helvetica Chimica Acta, vol. 69, pp. 438–441, 03/19/86.
Atta-ur-Rahman et al., Z. Naturforsch., 31b, pp. 1416–1420 (1976).
Döé de Maindreville et al., Bull. Soc. France, series II, No. 5–6, pp. II-179-II-183 (1981).
Kuehne et al., J. Org. Chem., vol. 46, No. 10, pp. 2002–2009 (05/08/81).
Kuehne et al., J. Org. Chem., vol. 46, No. 17, pp. 3443–3447 (08/14/81).
Kutney et al., Can. J. Chem., vol. 57, No. 13, pp. 1682–1690 (07/01/79).
Neuss et al., Tetrahedron Letters, No. 7, pp. 783–787 (1968).
Dorman et al., Chemical Abstracts, vol. 86; 72962p (1977).
Langlois et al., J. Am. Chem. Soc., vol. 98, No. 22, pp. 1717–1724 (10/27/76).
Langlois et al., Tetrahedron Letters, No. 14, pp. 1099–1102 (176).
Mangeney et al., J. Am. Chem. Soc., vol. 101, No. 8, pp. 2243–2245 (04/11/79).
Langlois et al., Helv. Chim. Acta, vol. 63, No. 4, pp. 793–805 (1980).
Kutney et al., Helv. Chim. Acta, vol. 58, No. 6, pp. 1690–1719 (1975).
Andriamialisoa et al., Tetrahedron, vol. 34(6), pp. 677–683 (1 1978).
Kunesch et al., Tetrahedron Letters, No. 52, pp. 5073–5076 (1979).
De Moraes, Thesis, Univ. of Rheims, France, (1982), pp. 22, 23, 48, 82.
Rosazza et al., NIH Publ., 1983, 83–2487, Cancer Treat Symp., pp. 51–58.
Kuehne et al., Chemical Abstracts, vol. 106:5293q (1987).
Sundberg et al., Chemical Abstracts, vol. 93:114797r (1980).
Guéritte et al., J. Org. Chem., vol. 46(26), pp. 5393–5395 (1981).
Marazano et al., Chemical Abstracts, vol. 95:25372x (1981).
Szantay et al., Chemical Abstracts, vol. 100:121422f (1984).

*Primary Examiner*—Robert Gerstl
*Assistant Examiner*—Diana G. Rivers
*Attorney, Agent, or Firm*—Jon S. Saxe; George M. Gould; William H. Epstein

[57] ABSTRACT

A new process for the stereospecific synthesis of alkaloids of the vinblastine and vincristine type including the synthesis of vinblastine and vincristine as well novel alkaloids which are active as anti-tumor agents.

48 Claims, No Drawings

SYNTHESIS OF VINBLASTINE AND VINCRISTINE TYPE COMPOUNDS

CROSS REFERENCE TO RELATED APPLICATIONS

This application is a continuation-in-part of U.S. application Ser. No. 810,112 filed Dec. 18, 1985, abandoned, Kuehne which in turn is a continuation-in-part of U.S. application Ser. No. 710,792 filed Mar. 12, 1985, abandoned, Kuehne.

BACKGROUND OF THE INVENTION

The indole-indoline alkaloids, the most important of which can be represented by the compound of formula I

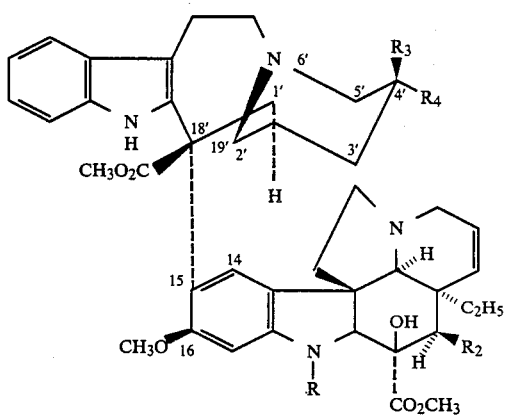

wherein $R_2$ is acetoxy or hydroxy; and R is formyl or methyl;-include vinblastine and vincristine, which are anti-tumor agents widely used in the treatment of cancer. These agents have been prepared from extracts of the Vinca rosea plant. As these alkaloids are present in the plant only in very small concentrations and since they must be separated from many other companion alkaloids, their synthetic generation becomes particularly valuable.

Preparation of compounds of formula I, by a pathway quite different from that of the present invention, has already been described. Thus Potier and Kutney obtained products with the C18'S-C2'R absolute configuration, which is critical for anti-tumor activity, by a coupling reaction of the $N^b$-oxide of catharanthine, or its derivatives, with vindoline, in the presence of trifluoroacetic anhydride, followed by a reduction reaction. [See Potier et. al. J. Am. Chem. Soc. 98. 7017 (1976) and Kutney et. al. Helv. Chim. Acta, 59, 2858 (1976)].

The Potier and Kutney coupling process has disadvantages. The yields are not satisfactory except for the coupling of catharanthine N-oxide with vindoline and even there the preparative yield is low. While vindoline is the most abundant alkaloid of Vinca rosea and is thus readily available, the other possible components of the Potier-Kutney coupling process (catharanthine, allocatharanthine, voacangine,) are relatively inaccessible, costly, and they do not allow a wide range of structural variation of that component of the coupling process.

SUMMARY OF THE INVENTION

In accordance with this invention it has been found that when compounds of the formula:

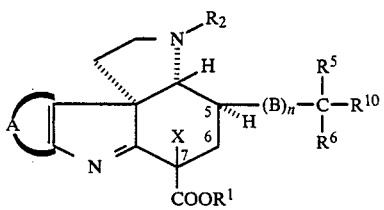

wherein n is an integer of 0 to 1; A is the remaining portion of an aromatic carbocyclic or heterocyclic ring; B is an alkylene chain of from 1 to 4 carbon atoms; $R^{10}$ is —$CH_2Y$, formyl or a formyl protected by formation of an acetal group; $R^1$ is lower alkyl and Y individually is a leaving group or a hydrolyzable ether group; X is halo and $R^2$ is amino protecting group; $R^5$ is hydrogen or lower alkyl; and $R^6$ is individually hydrogen, lower alkyl or a hydrolyzable ether group or taken together with Y forms lower alkylidenedioxy or oxo; with the proviso that when $R^6$ is a hydrolyzable ether group, and $R^{10}$ is —$CH_2Y$, Y is a leaving group; are condensed with a compound containing the ring system of vindoline or salt thereof, a compound of the formula:

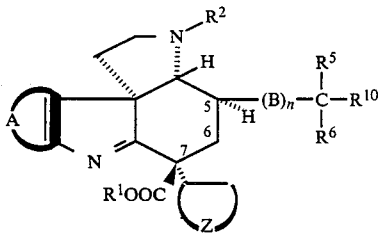

wherein Z is the residue of a vindoline ring system and n, A, B, $R^1$, $R^2$, $R^5$, $R^6$ and $R^{10}$ are as above; with the proviso that when $R^6$ is a hydrolyzable ether group, and $R^{10}$ is —$CH_2Y$, Y is a leaving group; or mixtures thereof with the corresponding 7R diastereoisomer having the opposite configuration at the 5-position, are formed.

Unexpectedly, it has been found that this condensation produces the correct relative configuration of the asymmetric carbon atoms at C7 and C5 in the compound of formula III, to produce alkaloids of the formula I having the absolute configuration at the asymmetric carbon atoms 18' and 2' as shown. This absolute configuration is critical for anti-tumor activity. Through the process of this invention one can ultimately produce compounds of the formula

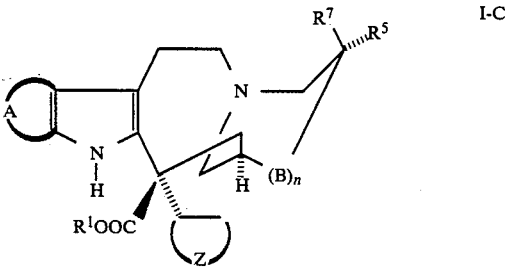

wherein n, A, B, Z and $R^1$ are as above; and $R^5$ is hydrogen or lower alkyl; and $R^7$ is hydrogen, hydroxy or lower alkyl; which have the "natural" conformational structure i.e. that of the alkaloids isolated from plants. It is these alkaloids of the "natural" configuration which are active as anti-tumor agents. In addition to these "natural type" alkaloids, the process of this inventions produces for the first time alkaloids of the formula

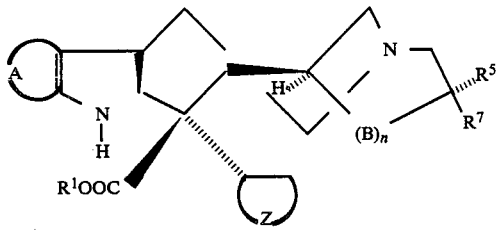

I-B where n, A, B, Z, $R^1$, $R^5$ and $R^7$ are as above; which have a conformational structure different from the "natural type" conformational structure. In accordance with this invention the compounds of formula I-B are intermediates for the "natural type" compounds of formula I-C and can be converted to the compounds of formula I-C by heating. While the compounds of formula I-B are not by themselves active as anti-tumor agents, they may be administered as "pro-drugs" and activated by transformation into the compounds of formula I-C at the tumor site by heating or by micro waves or by ultrasonics or by infra-red radiation.

Through the stereospecific nature of the formation of the compound of formula III, one can produce the known anti-tumor agents;

vinblastine—the compound of formula I where $R_2$ is acetoxy, R is methyl, $R_3$ is hydroxy, $R_4$ is ethyl; and vincristine—the compound of formula I where $R_2$ is acetoxy, $R_3$ is hydroxy, $R_4$ is ethyl, and R is formyl.

In addition, this synthesis provides a method for producing new vincristine and vinblastine type compounds which are active as anti-tumor agents, since it provides the correct relative and absolute configuration of the asymmetric carbon atoms at C18' and C2' respectively. Therefore, through the process of this invention not only can the known vincristine and vinblastine alkaloids be synthesized, but also new anti-tumor compounds having the following formula:

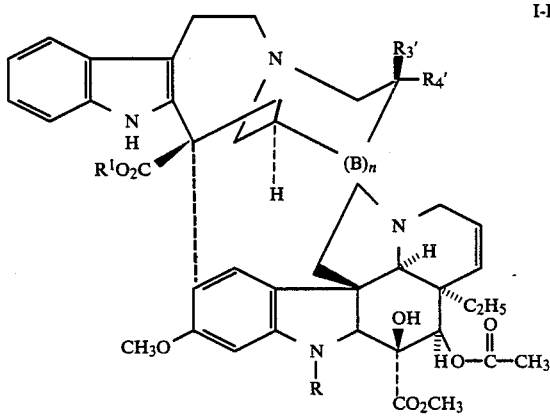

I-D wherein n, B, R and $R^1$ are as above; $R_3'$ is hydrogen, hydroxy or lower alkyl; $R_4'$ is hydrogen or lower alkyl; and R is formyl or methyl with the proviso that when n is 1, B is methylene and one of $R_3'$ or $R_4'$ is ethyl; the other of said $R_3'$ or $R_4'$ is lower alkyl. Where $R_3'$ in the compound of formula I-D is hydroxy, this hydroxy group can be etherified in a conventional manner to form a compound of formula I-D where $R_3'$ is a hydrolyzable ether. These compounds are also active in the same manner as the compound of formula I-D.

Among the compounds of Formula I-D where $R^{1'}$ is methyl, B is methylene and n is 1, the following are preferred:

Compound A=the compound of the formula I-D where R is methyl and $R_4'$ is methyl and $R_3'$ is hydrogen.

Compound B=the compound of formula I-D where R is methyl and $R_3'$ and $R_4'$ are hydrogen.

Compound C=the compound of formula I-D where R is formyl, and $R_4'$ is methyl and $R_3'$ is hydrogen.

Compound D=the compound of formula I-D where R is formyl, and $R_3'$ and $R_4'$ are hydrogen.

Compound E=the compound of formula I-D where R is formyl, $R_4'$ is n-propyl and $R_3'$ is hydrogen

DETAILED DESCRIPTION

The compounds of the formula I and I-C and I-D and their pharmaceutically acceptable salts are useful in inhibiting the growth of malignant tumors and may be utilized in this same manner as vinblastine and vincristine. However, the new analogues and conformational isomers of vinblastine and vincristine produced through the claimed synthesis of this invention such as the compounds of I-D, in particular Compound A, B, C, D and E, do not have the high toxicity of vincristine and vinblastine as will be seen from the results of Table 1 below.

The effect of Compounds A and B on intraperitoneally transplanted tumors and their reduced toxicity can be seen from the results of the P-388 leukemia test. In this test the compounds were administered in a saline solution. The P-388 leukemia test was performed on BDF hyrid mice. The tests were carried out on groups of six mice and $10^6$ tumor cells/animal were transplanted intraperitoneally. Administration of the test compounds was started in the 24th hour after transplantation. Treatment was performed intraperitoneally and the body weight and state of animals was determined every day. The effect obtained on the treated animals is expressed in % of the mean length of life of the control group, given in days. This increase over the control is expressed in Table 1 as %T/C, i.e. Treated/Control. The figures in parenthesis represent repeat determinations two months after the first determination.

TABLE I

| Compound | Dose (mg/kg) | Schedule | % T/C | Wt. loss (Day 5) grams/Mouse |
|---|---|---|---|---|
| Compound A | | | | |
| (a) Free Base | | | | |
| | 2 | Day 1 | 119 | None |
| | 2.5 | Days 1, 5, 9 | 118 | None |
| | 4.0 | Days 1, 5, 9 | 135 | None |
| | 10.0 | Days 1, 5, 9 | 207 | 0.4 |
| (b) HCl Salt | 2 | Day 1 | 106 | None |
| | 2 | Days 1, 5, 9 | 115 | None |
| | 5 | Days 1, 5, 9 | 181 | None |
| Compound B | | | | |
| | 50 | Days 3, 8 | 113 | None |
| | 100 | Days 3, 8 | 251 | None |
| Vincristine | 1 | Day 1 | 126 (139) | 2.2 |

TABLE I-continued

| Compound | Dose (mg/kg) | Schedule | % T/C | Wt. loss (Day 5) grams/Mouse |
|---|---|---|---|---|
| positive control | 1 | Days 1, 5, 9 | 152 (219) | 1.3 |

The tumor inhibitory effect of the new compounds on P-388 mouse tumor is evident at doses ranging from 0.01 to 100 mg/kg/day dose and is equal to the effect of the known indole-indoline alkaloids. At the same time, the instant compounds are less toxic than these known alkaloid compounds.

For human treatment the compounds can best be employed intravenously or as infusions.

In utilizing the novel compounds of formula I, I-C and I-D as anti-tumor agents in mammals, the parenteral route is ordinarily employed. Prior to administration, the drug is customarily mixed with a pharmaceutically suitable carrier. With parenteral administration, the intravenous route is preferred although, with smaller mammals such as mice, the intraperitoneal route may be used. For intravenous administration, isotonic solutions containing 1–10 mg/mL. of a salt of an alkaloid of the formula I or salts thereof are employed. The drug is administered at a dose of from 0.01 to 10 mg/kg and preferably from 0.05 to 1 mg/kg of human body weight once or twice a week or every two weeks depending on both the activity and the toxicity of the drug. An alternative method of arriving at a therapeutic dose is based on body surface area with a dose in the range 0.1 to 10 mg/meter squared of human body surface administered twice weekly or every 7 or 17 days.

As would be expected, the novel compounds encompassed within formula I or I-D differ in their anti-tumor spectrum from that of vinblastine and vincristine as the anti-tumor spectra of those compounds differ among themselves, one drug being more effective against certain tumors or classes of tumors and less effective against others. However, in utilizing these compounds clinically, an oncologist may administer them initially by the same route, in the same vehicle and against the same types of tumors as employed clinically with vincristine and vinblastine. Differences in dosage level would, of course, be based on relative oncolytic potency and toxicity.

Tumors against which clinical trial candidates are screened include adenocarcinoma of the breast, adenocarcinoma of the colon, bronchogenic carcinoma, adenocarcinoma of the pancreas, ovarian cancer, malignant melanoma, acute myelocytic leukemia, acute lymphocytic leukemia, lymphomatous disease and malignant glioma. A compound of formula I would be tested clinically against one or more of these tumors as well as other tumors known to be susceptible to i.v. administration of vincristine and vinblastine. After its potency, nature and degree of side effects etc. had been established, the drug would be tried against tumors for which there is no therapy. After preliminary tests were concluded and the results published, the drug would be used against tumors susceptible to its action at relatively non-toxic dose levels.

Useful non-toxic acids for forming acid addition salts with the bases of formula I include inorganic acids such as hydrochloric acid, nitric acid, phosphoric acid, sulfuric acid, hydrobromic acid, hydroiodic acid, phosphorous acid and the like, as well as salts of non-toxic organic acids including aliphatic mono and dicarboxylates, phenyl-substituted alkanoates, hydroxy alkanoates and alkandioates, aromatic acids, alphatic and aromatic sulfonic acids, etc. Such pharmaceutically acceptable salts thus include the sulfate, bisulfate, sulfite, bisulfate, nitrate, phosphate, monohydrogenphosphate, dihydrogen-phosphate, metaphosphate, phosphite, pyrophosphate, chloride, bromide, iodide, acetate, propionate, decanoate, caprylate, acrylate, formate, isobutyrate, caproate, heptanoate, propionate, oxalate, malonate, succinate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzene-sulfonate, toluenesulfonate, chlorobenzenesulfonate, xylenesulfonate, phenylacetate, phenylpropionate phenylbutyrate, citrate, lactate, 2-hydroxybutyrate, glycollate, maleate, tartrate, methanesulfonate, propane-sulfonate, naphthalene-1-sulfonate, naphthalene-2-sulfonate and the like salts.

In carrying out the reaction to produce the compound of formula II the substituent A in the compound of formula II can be any group which when connected to the ring system of the compound of formula II forms an aromatic carbocyclic or hetercyclic ring. Any conventional aromatic carbocyclic or heterocyclic ring structure can be formed by A. The aromatic carbocyclic ring substrates formed by A include the carbocyclic aromatic monocyclic or polycyclic ring structures containing 6 to 12 carbon atoms in the ring, most preferably benzene and naphthalene. Where A, when connected to the remainder of the molecule in the compound of formula II forms an aromatic heterocyclic ring structure, any aromatic heterocyclic ring structure can be formed including those ring structures which contain from 1 to 3 nitrogen or sulfur atoms as the only hetero atoms in the ring structure. The heterocyclic ring structure is preferably monocyclic or bicyclic and can contain from 5 to 10 members in its ring. Among the aromatic heterocyclic ring structures formed by A are included pyridine, quinoline, pyrrole, thiophene etc.

The ring structure formed by A can be unsubstituted or substituted with any conventional substituent. The use of these substituents does not prevent the overall reaction to produce the compound of formula III with the stereo configuration of vinblasine. If the ring formed by A is substituted, it can be substituted bY any conventional substituent such as lower alkyl, lower alkoxy, hydroxy, carboxy, lower alkoxycarbonyl, lower alkoxy lower alkyl, lower alkoxycarbonyl lower alkyl, amino, nitro, lower alkylamino, halo, etc.

In the process of this invention B can be any alkylene chain of from 1 to 4 carbon atoms such as methylene, ethylene, propylene, butylene. The lower alkylene chain can be unsubstituted or substituted with any conventional substituent including those substituents mentioned hereinbefore in connection with the ring defined by A. Among the most preferred substituents are included hydroxy, lower alkyl, lower alkoxy, etc.

The term lower alkylidenedioxy designates a lower alkylidenedioxy substituent where lower alkylidene contains from 1 to 7 carbon atoms. Among the preferred lower alkylidenedioxy substituents are included isopropylidenedioxy.

Where $R^{10}$ is a formyl group protected through the formation of an acetal, the acetal can be formed with any conventional alcohol or glycol to produce an acetal which upon hydrolysis yields $R^{10}$ as formyl. Among the conventional alcohols used to produce the acetals are the mono-hydroxy alcohols such as methanol and ethanol as well as other lower alkanols and dihydroxy alcohols, or glycols which produce cyclic acetals such as lower alkylene glycols including ethylene glycol, etc and dihydroxy lower alkanes containing 2 to 7 carbon atoms such as 1,3-dihydroxypropane, 1,4-dihydroxy butane, etc.

The hydrolyzable ether groups can be any ether protecting groups, which when subjected to cleavage form a hydroxy group. A suitable ether protecting group is, for example, the tetrahydropyranyl ether, or 4-methyl-5,6-dihydro-2H-Pyranyl ether. Others are arylmethyl ethers such as benzyl, benzylhydryl, or trityl ethers or alpha-lower alkoxy lower alkyl ether, for example, methoxymethyl, or tri(lower alkyl)silyl ethers such as trimethyl silyl ether or dimethyl-tert-butyl silyl ether. The preferred ethers which are removed by acid catalyzed cleavage are t-butyl and tetrahydropyranyl and the tri(lower alkyl)silyl ethers, particularly dimethyl-tert-butyl silyl ether, which may be removed by reaction with a fluoride such as tetrabutyl ammonium fluoride. Acid catalyzed cleavage is carried out by treatment with a strong organic or inorganic acid. Among the preferred inorganic acids are the mineral acids such as sulfuric acid, hydrohalic acid, etc. Among the preferred organic acids are lower alkanoic acids such as acetic acid, para-toluene sulfonic acid, etc. The acid catalyzed cleavage can be carried out in an aqueous medium or in an organic solvent medium. Where an organic acid is utilized, the organic acid can be the solvent medium. In the case of t-butyl ethers, an organic acid is generally utilized with the acid forming the solvent medium. In the case of tetrahydropyranyl ethers, the cleavage is generally carried out in an aqueous medium. In carrying out this reaction, temperature and pressure are not critical and this reaction can be carried out at room temperature and atmospheric pressure.

The leaving group can be any conventional leaving group. Among the conventional leaving groups which are preferred are tosyloxy, mesyloxy and halogen. With respect to $R^2$, which is an amino protecting group, any conventional amino protecting group which can be removed by hydrogenolysis or photochemical cleavage can be utilized in accordance with this invention. Among the preferred amino protecting groups are included trityl, o-nitrobenzyl, benzyl, and diphenylmethyl, etc.

As used throughout this application the term "lower alkyl" designates monovalent saturated straight or branched chain alphatic hydrocarbon groups containing from 1 to 7 carbon atoms such as ethyl, methyl, n-propyl, isopropyl, n-butyl, isobutyl. The term "lower alkylene" designates a divalent saturated aliphatic straight or branched chain hydrocarbon radical containing 1 to 4 carbon atoms such as methylene or ethylene. The term "halogen" or halide includes all four halogens or halides such as chlorine, bromine, fluorine and iodine with chlorine, bromine and iodine being preferred. The term "lower alkanoyl" designates alkanoyl groups derived from alphatic monocarboxylic acids containing from 1 to 7 carbon atoms such as acetyl, butyryl, Pivaloyl, etc.

In condensing the compound of formula II with a compound containing the ring system of vindoline, one produces the compound of formula III with the configurations as shown at the 5 and 7 positions, which are necessary for obtaining vinblastine type compounds.

The compound of formula III with the configuration as shown can be produced as a mixture thereof with the corresponding diastereoisomer having the opposite stereo-configuration at the 5 and 7 positions from that shown, depending upon the stereo-configuration at the 5 position of the compound of formula II. If the compound of formula II has a 5 configuration as shown, condensation of the compound of formula II with a compound containing the vindoline ring system will produce the compound of formula III with the configuration at the 5 and 7 positions as shown. On the other hand, if the compound of formula II contains a mixture of 5S and 5R isomers, the compound of formula III will be formed as a mixture of the 7 diastereoisomer as shown, with the corresponding diastereoisomer having the opposite configuration at both the 7 and 5 positions to that shown. Through the process of this invention, even with a mixture of enantiomers of formula II, one can produce the compound in formula III only as a mixture of the aforementioned diastereoisomers. This allows one to synthesize the vinblastine type compound of formula I with the correct stereo-configuration. If one utilizes a 5R,S diastereoisomic mixture of the compound of formula II, the compound of formula III is produced as a mixture of the 7S diastereoisomer as shown with the corresponding 7R diastereoisomer having the opposite configuration at the 5-position to that shown. This diastereoisomic mixture can be separated either at this stage or at some later stage in the reaction scheme utilizing conventional means such as chromatography.

In carrying out the condensation of the compound of formula II with a compound containing the ring system of vindoline, any organic compound which contains the structure shown in formula II can be utilized. It has been found that compound of formula II, when condensed with compounds containing the ring system of vindoline or salts thereof, produce the compound of formula III with the specific stereoconfiguration about the 5 and 7 position shown therein. Therefore, the substituents on A and B, as well as the substituents on the ring system of vindoline do not interfere with the reaction of this invention. These substituents will be carried along to produce the compounds of formula III with stereo-configuration about the 5 and 7 position set forth above. In accordance with this invention any compound containing the ring system of vindoline can be condensed with the compounds of formula II to produce the compounds of formula III. Among the preferred compounds which contain the ring system of vindoline for use in this invention are vindoline, 16-lower alkoxy-vindoline and 16-methoxy-2,3-dihydro $N^a$ methyl-tabersonine.

The condensation of the compound of formula II with a vindoline ring system containing compound or salts thereof is carried out in the presence of an aprotic solvent. In carrying out this reaction any conventional aprotic solvent can be utilized. Among the conventional aprotic solvents are aldehydes and ketones such as acetone, methyl ethyl ketone, etc. Other aprotic solvents which are also preferred include ethers such as dioxane and diethyl ether. In accordance with a preferred embodiment of this invention, this reaction takes place in the presence of a protic acid or with a salt of a vindoline ring system containing compound with a protic acid. Any conventional protic acid can be used in carrying out this reaction. Among the preferred protic acids are hydrohalic acids such as HCl and HBr as well as acids such as HBF₄. In carrying out this reaction it is also generally preferred that condensation take place in the presence of a silver salt. Any conventional silver salt which reacts with halides can be utilized in carrying out this reaction. Among the preferred silver salts are silver nitrate, silver fluoroborate, silver perchlorate. In carrying out this reaction, temperature and pressure are not critical and this reaction can be carried out at room temperature and atmospheric pressure. On the other hand, higher or lower temperatures can be utilized. Generally it is preferred to carry out this reaction at a temperature of from $-10°$ C. to $+20°$ C.

The compound of formula III can be converted to a compound of the formula

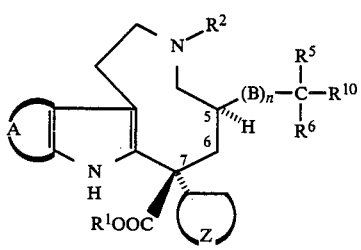

V wherein n, A, B, Z, $R^{10}$, $R^1$, $R^2$, $R^5$, $R^6$ and $R^{10}$ are as above; with the proviso that when $R^6$ is a hydrolyzable ether group, $R^{10}$ is —CH₂Y and Y is a leaving group. This conversion if carried is carried out by treating the compound of formula III with an alkali metal borohydride in an acid. Any conventional acid can be used in this conversion. Among the acids are included inorganic acids such as phosphoric acid, sulfuric acid as well as organic acids such as formic acid and acetic acid, with organic acids such as acetic acid being preferred. In carrying out this reaction, the organic acid can be utilized as the solvent. Furthermore, in carrying out this reaction, temperature and pressure are not critical and this reaction can be carried out at room temperature and atmospheric pressure. On the other hand, if desired elevated or lower temperatures can be utilized.

In accordance with another embodiment of this invention the compound of formula V can be produced by condensing a compound of the formula

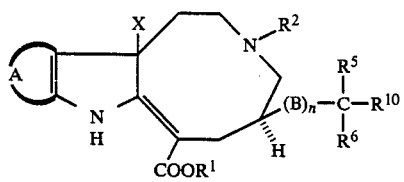

II-B wherein n, X, B, Y, $R^1$, $R^2$, $R^5$, $R^6$ and $R^{10}$ are as above; with a compound containing the ring system of vindoline. This reaction can be carried out utilizing the same conditions described hereinbefore in connection with the conversion of a compound of formula II to a compound of formula III. However, it is generally preferred to carry out this reaction, without the presence of a silver salt, simply in the presence of an inert solvent. Generally it is preferred to carry out this reaction in a protic solvent in the presence of an acid, or in an acid halide. In carrying out this reaction with an acid, any protic solvent such as a lower alkanol i.e., methanol or ethanol can be utilized. The acids which are generally utilized are the organic acids such as the lower alkanoic acids i.e. acetic acid. On the other hand mineral acids such as hydrochloric acid can be utilized as well. If this reaction is carried out in an acid halide, any conventional acid halide can be used such as lower alkanoic acid halides, i.e. acetyl chloride. In these procedures, temperature and pressure are not critical and room temperature can be utilized.

In the next step of this process the compound of formula V where $R^6$ is hydrogen, lower alkyl, or hydrolyzable ether is converted to the compound of the formula

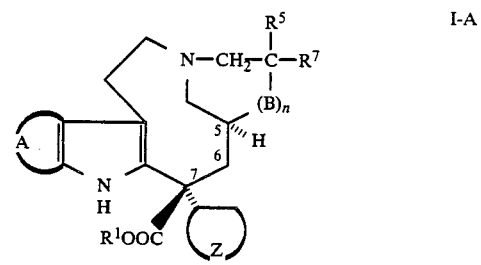

I-A where n, $R^1$, A, $R^5$, Z, B, and $R^7$ are as above.

The compound of formula V where $R^{10}$ is —CH₂Y and Y is a leaving group or taken together with $R^6$ forms oxo can be converted to the compound of formula I-A by first subjecting the compound of formula V to hydrogenolysis or photochemical cleavage depending upon the substituent $R^2$. In this manner the compound of formula V where $R^2$ is hydrogen is produced. In carrying out this reaction any conventional method of hydrogenolysis or photochemical cleavage to remove an amino protecting group can be utilized.

In producing the compound of formula I-A, the compound of formula V where $R^2$ is hydrogen and $R^{10}$ is —CH₂Y and Y is a leaving group, or taken together with $R^6$ forms oxo can be cyclized in an organic solvent at a temperature of $10°$ C. to $100°$ C. In carrying out this reaction any conventional hydrocarbon or ether solvent can be utilized with aromatic solvents such as toluene or benzene being preferred. If elevated temperatres are required, lower boiling solvents can be utilized. With these lower boiling solvents the cyclization occurs by heating in a sealed tube. Where $R^6$ taken together with Y forms oxo in the compound of formula V, the compound of formula I-A is formed where $R^7$ is hydroxy.

In accordance with an alternative embodiment the compound of the formula V where $R^{10}$ is —CH₂Y and Y is a leaving group or taken together with $R^6$ forms oxo is converted to the compound of formula I-A via an intermediate of the formula

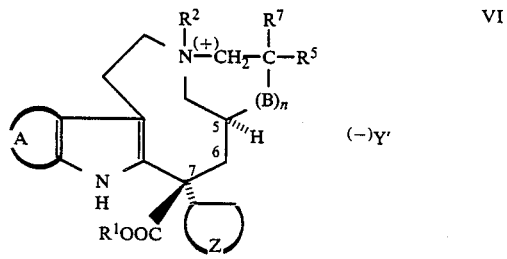

VI wherein n, $R^1$, $R^2$, A, $R^5$, Z and B are as above $R^7$ is hydrogen, hydroxy or lower alkyl and Y' is an anion.

In producing the compound of formula VI, the compound of formula V where $R^{10}$ is CH₂Y and Y is a leaving group or taken together with $R^6$ forms oxo is heated in a organic solvent to a temperature of from 35° C. to 100° C. In carrying out this reaction, any conventional inert organic solvent can be utilized with aromatic hydrocarbons such as toluene and benzene or ether solvents or lower alkanols such as methanol being preferred. Among the solvents which can be utilized are solvents boiling above 35° C. However, lower boiling solvents can also be utilized if the reaction is carried out in a sealed tube. The leaving group Y in this reaction becomes the anion Y' upon formation of the quaternary salt. Where $R^6$ in the compound of formula V is a hydrolyzable ether group, the compound of formula VI is formed where $R^7$ is a hydrolyzable ether group. The compound of formula VI is converted to the compound of formula I-A by removal of the amino protection group as described above and removal of the hydroxy protecting ether group through conventional hydrolysis. Either the ether hydroxy protecting group or the amino protecting group may be removed first, depending upon the conditions utilized for removing these groups.

The compound of formula V where $R^{10}$ is $-CH_2 Y$ and Y is a hydrolyzable ether group can be converted to the compound of formula V, where $R^{10}$ is a methylene substituted with a leaving group, by first removing the ether group by conventional ether hydrolysis to produce the compound of formula V where Y is $-OH$. This compound of formula V where Y is a hydroxy can be converted to the compound of formula V when Y is a leaving group such as mesyloxy, tosyloxy, or halogens such as chlorine or iodine by any conventional method of converting a hydroxy group to a leaving group. The compound of formula V where Y is a leaving group produced as above is converted to the compound of formula I-A as described above.

The compound of formula V where $R^{10}$ is $-CH_2 Y$ and Y and $R^6$ form a lower alkylidenedioxy, particularly isopropylidenedioxy, can be converted to the compound of formula I-A by first converting this compound to the corresponding compound of formula V where $R^2$ is hydrogen. This conversion is carried out by removing the amino protecting group as described above. After the amino protecting group has been removed the lower alkylidenedioxy groups may be removed by hydrolysis to produce the compound of formula V where $R^{10}$ is $-CH_2OH$, $R^2$ is hydrogen and $R_6$ is hydroxy. On the other hand, this compound can be produced from the compound of formula V where $R^{10}$ is $-CH_2 Y$ and Y and $R_6$ form lower alkylidenedioxy by first hydrolyzing the lower alkylidenedioxy groups to produce the compound of formula V where $R^2$ is an amino protecting group, $R^{10}$ is $-CH_2OH$ and $R^6$ is $-OH$ and thereafter removing the amino protecting group. The compound of formula V when $R^2$ is hydrogen, $R^{10}$ $-CH_2OH$ and $R^6$ is OH can be converted to the compound of formula I-A by cyclization with a cyclization agent such as methyl triphenoxyphosphonium halide. Any of the conditions conventionally used with these agents can be utilized in this conversion.

In the compound of formula V where $R^{10}$ is an acetalized formyl group, this compound can be converted to the compound of formula I-A by first hydrolyzing the acetal group, by conventional acetal hydrolysis, to produce the corresponding compound of formula V where $R^{10}$ is formyl. This latter compound is next converted to the corresponding compound of formula V where $R_{10}$ is formyl, and $R^2$ is hydrogen by removal of the amino protecting group in the manner described hereinabove. On the other hand this compound can be produced by first removing the amino protecting group and thereafter hydrolyzing the acetal group. The compound of formula V where $R^2$ is hydrogen and $R^{10}$ is formyl can be converted to the compound of formula I-A by first heating to a temperature of from 35° C. to 100° C. in a lower alkanoic acid followed by reduction with sodium cyanoborohydride in a lower alkanoic acid at temperatures of from 20° C. to 60° C.

The compound of formula V where $R^2$ is hydrogen and $R^{10}$ is formyl when subjected to heating in a lower alkanoic acid forms a compound of the formula:

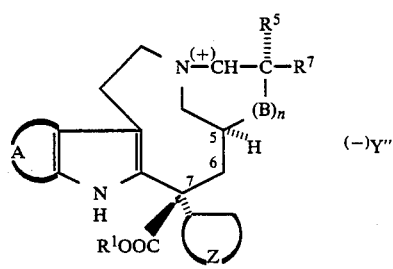

VII wherein n, $R^1$, A, $R^5$, Z, B, and $R^7$ are as above, and Y'' is an anion of a lower alkanoic acid. In forming the compound of formula VII, any lower alkanoic acid can be utilized, with a acetic acid and formic acid being especially preferred. The compound of formula VII can be converted to the compound of formula I-A by reduction with sodium cyanoborohydride in a lower alkanoic acid at a temperature of from 20° C. to 60° C.

If the compound of formula V where $R^{10}$ is formyl, at least one of $R^5$ and $R^7$ is hydrogen, is heated to a temperature of 35° C. to 100° C. in a neutral or basic solvent the following compound is formed:

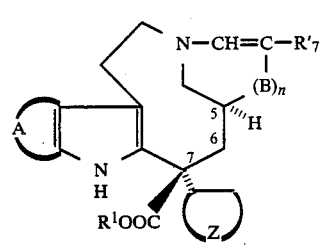

VII-A where n, A, Z, B and $R^1$ are as above and $R'_7$ is hydrogen or lower alkyl.

On the other hand if the compound of formula V where $R^{10}$ is formyl, and both of $R_5$ and $R_7$ are lower alkyl, is heated to a temperature of 35° C. to 100° C. in a neutral or basic organic solvent then a compound of the formula

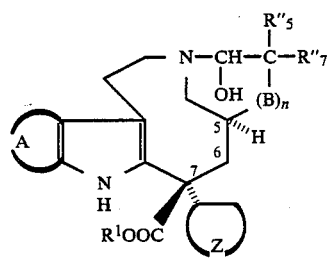

VII-B where A, $R^1$, n, Z and B are as above, and $R_5''$ where $R_7''$ are individually lower alkyl; is formed. The compounds of formula VII-A and VII-B can be converted to the corresponding compounds of formula I-A by reduction in the same manner as described in connection with the conversion of the compound of formula VII into the compound of formula I.

In forming the compound of formula VII-A or VII-B, any conventional neutral or basic organc solvent can be used or, if desired, mixtures of neutral and basic solvents. Among the preferred neutral solvents which can be utilized are included toluene, benzene, trichloromethane, etc. Among the preferred basic solvents are included pyridine, triethylamine, etc.

The compounds of formulae III, V, VI, VII, VII-A and VII-B and I-A can be formed as either the 7S-diastereomer with the C5 configuration as shown or as a mixture thereof with its corresponding 7R diastereoisomer where the configuration at C5 is opposite to that shown. The formation of the 7S-diastereomer or its mixture with the corresponding 7R-diastereomer depends upon enantiomeric purity of the compound of formula II at the tertiary carbon attached to the tertiary nitrogen group contained therein. If a mixture of the 7S-diastereomer with the corresponding 7R-diastereomer is formed these diastereoisomers can be separated at any stage of the process by means of chromatography. In each instance, the stereochemistry at C5 will correspond uniquely to the stereochemistry at C7 and have the priority anti-reflective relationship (PARF) found in vinblastine.

The compound of formula I-A can exist as one or the other or as a mixture of both of two conformational isomers, i.e. a compound of the formula I-B and I-C. The compound of formula I-C has the conformational structure of the natural product.

In accordance with this invention we have found that when a compound of structure I-B is heated at a temperature of from 30° C. to 150° C. it is converted to a compound having the natural conformational structure, i.e. a compound of the formula I-C. In carrying out this reaction, any conventional inert organic solvent can be utilized but this conformational conversion of I-B to I-C can be obtained in any medium. In fact heating the compound of formula I-B in solid form will accomplish this result. If a solvent is desired, the preferred solvents are the aliphatic or aromatic hydrocarbons boiling above 30° C. Among these solvents are included toluene and benzene. On the other hand, a mixture of compounds of formula I-B and I-C can be converted to the "natural" conformational isomer by heating in the manner described above. If it is desired to obtain the compound of formula I-B in pure form, the compound of formula I-B can be separated from its mixture with the compound of formula I-C. Any conventional method of separation can be used to separate the compound of formula I-B from this mixture of conformational isomers.

In preparing the novel compounds of formula I-D, intermediates of formula V are produced where n, A, B, Z, $R^1$, $R^2$, $R^5$, $R^6$ and $R^{10}$ are as above with the proviso that when n is 1, B is methylene and one of $R^5$ and $R^6$ are ethyl, the other of $R^5$ and $R^6$ is lower alkyl. Also, in preparing the novel compound of formula I-D, the intermediates of formula I-A, VI and VII are produced where n, A, B, Z, $R^1$, $R^2$, $R^5$, $R^6$ and $R^{10}$ are as above, with the proviso that when n is 1, B is methylene, and one of $R^5$ and $R^7$ is ethyl, the other of said $R^5$ and $R^7$ is lower alkyl.

The intermediates of formula VII-A used for preparing the novel compounds of formula I-D are those compounds where n, A, B, Z, $R^1$, and $R'^7$ as above, with the proviso that $R_7'$ is other than ethyl.

The compound of formula II is prepared by reacting a compound of the formula

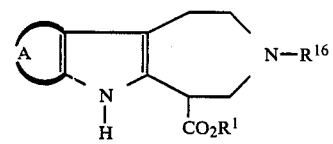

XII wherein A and $R^1$ are as above; and $R^{16}$ is hydrogen or an amino protecting group; with any one of the following compounds:

XIII-A $$R_5 \begin{matrix} (B)_n \\ \diagup \diagdown \\ O \end{matrix} OH$$

XIII-B $$O=CH-CH_2-(B)_n-\underset{\underset{R^{11}}{|}}{\overset{\overset{R^5}{|}}{C}}-CO_2R^7$$

XIII-C $$CH_2 \underset{\underset{R_{12}}{\diagdown \diagup}}{\overset{R^5}{\overset{|}{C}}} -(B)_n-CH_2-CHO$$

XIII-D $$O=CH-CH_2-(B)_n-\underset{\underset{R^{11}}{|}}{\overset{\overset{R^5}{|}}{C}}-CH_2-OV$$

wherein n, $R_5$, $R_7$ and B are as above; $R^{11}$ is hydrogen or lower alkyl; and $R_{12}$ is lower alkylidenedioxy or oxo and V taken with its attached oxygen atoms forms a hydrolyzable ether group.

The compound of formula XII where $R^{16}$ is hydrogen can be reacted with the compound of formula XIII-A where $R_5$ is hydrogen or the compound of formula XIII-B or XIII-C where $R_{12}$ is lower alkylidenedioxy or the compound of formula XIII-D to produce a compound of the formula

XIII where n, A, B, $R^1$, V and $R^5$ are as above; $R^{15}$ is —CH$_2$—$R^9$ or —CO$_2$ $R^{13}$; $R^8$ is hydrogen, or lower alkyl; $R^9$ is hydroxy; or-OV or taken together with $R^8$ forms lower alkylidenedioxy and $R^{13}$ is lower alkyl, with the proviso that when $R^9$ is hydroxy, $R^5$ and $R^8$ are hydrogen.

In the compound of formula XIII-D, V can form any conventional hydrolyzable ether group with benzyl or tri(lower alkyl)silyl ethers being preferred.

The reaction of the compound of formula XII, with $R^{16}$ being hydrogen, with one of the compounds of formula XIII-A where $R^5$ is hydrogen, XIII-B or XIII-C where $R_{12}$ is lower alkylenedioxy to form the compound of formula XIII is carried out by a Mannich reaction. Any of the conditions conventional in Mannich reactions can be utilized in carrying out this reaction to form the compound of formula XIII. The reaction of this compound of formula XII with the compound of formula XIII-A produces the compound of formula XIII where $R^5$ and $R^8$ are hydrogen, $R^{15}$ is —$CH_2R_9$ and $R^9$ is hydroxy. The reaction of the compound of formula XII with the compound of formula XIII-B produces the compound of formula XIII where $R^5$ is hydrogen or lower alkyl; $R^8$ is hydrogen or lower alkyl and $R^{15}$ is —$CO_2R^{13}$. The reaction of the compound of formula XII with the compound of formula XIII-C produces the compound of formula XIII where $R^5$ is hydrogen or lower alkyl, $R^{15}$ is —$CH_2$ $R^9$ where $R^9$ and $R^8$ form lower alkylenedioxy. The reaction of the compound of formula XII with the compouund of formula XIII-D produces the compound of formula XXIII where $R^{15}$ is —$CH_2R^9$ and $R^9$ is —OV.

The compound of formula XIII is converted to the compound of formula II via the following intermediates

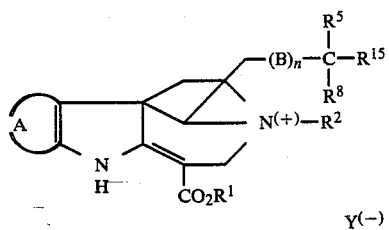

XIV

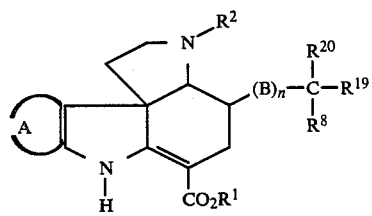

XV

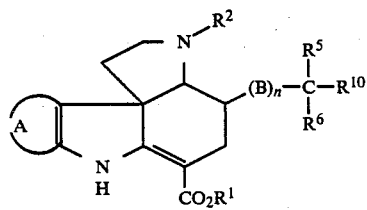

XVI wherein n, Y', A, B, $R^1$, $R^2$, $R^5$, $R^6$, $R^8$, $R^{10}$ and $R^{15}$ are as above; and $R^{20}$ is —$CH_2$ $R^{19}$ or —$CO_2$ $R^{13}$; $R^{13}$ is lower alkyl; $R^{19}$ is hydroxy or —OV or taken together with $R^8$ forms lower alkylidenedioxy or oxo; with the proviso that when $R^6$ is a hydrolyzable ether group, $R^{10}$ is —$CH_2Y$, and Y is a leaving group.

The compound of formula XIII is converted to the compound of formula XIV by protecting the tertiary amine group. Any conventional method of protecting a tertiary amine group with any of the aforementioned tertiary amine protecting groups which can be removed by hydrogenolysis or by photochemical cleavage can be utilized to carry out the conversion of formula XIII to the compound of formula XIV. In the formation of the compound of formula XIV, generally the amino protecting reagent containing a leaving group such as halide is reacted with the compound of formula XIII. This leaving group becomes the anion $Y^{31}$.

The compound of formula XIV is converted to the compound of formula XV by treating the compound of formula XIV with a amine or inorganic base. Any conventional amine base, such as tri-lower alkylamine particularly triethylamine and diisopropylethylamine or an inorganic base such as sodium carbonate can be utilized. This reaction can be carried out in any conventional inert organic solvent. Among the preferred organic solvent are the alcohols, such as the lower alkanols including methanol. In carrying out this reaction, temperature and pressure are not critical. This reaction can be carried out at room temperature and atmospheric pressure. On the other hand, higher or lower temperatures can be utilized. Generally it is preferred to carry out this reaction at the reflux temperature of the solvent.

On the other hand, when in the compound of formula XII, $R^{16}$ is an amino protecting group, condensation via a Mannich reaction with anyone of the compounds of formula XIII-A, XIII-B, XIII-C or XIII-D produces the compound of formula XVI directly. The use in this reaction of the compound of formula XIII-C where $R^{12}$ is oxo produces the compound of formula XV where $R^8$ and $R^{19}$ forms oxo.

The compound of formula XV where $R^{20}$ is —$CH_2$ $R^{19}$ and $R^9$ is hydroxy can be converted to the compound of formula XVI where $R^{10}$ is $CH_2$ Y where Y is a hydrolyzable ether group by conventional etherification procedures. Among the preferred ether groups are the benzyloxy, tri(lower alkyl silyl)oxy groups particularly t-butyldimethylsilyloxy. The hydroxy group can also be converted into a leaving group, such as mesyloxy, tosyloxy or a halide, particularly a chloride, bromide or iodide group, to produce the compound of formula XVI where Y is a leaving group. Reactions conventional for converting primary alcohols into the aforementioned leaving groups can be utilized to affect this conversion to form the compound of formula XVI.

Where $R^{20}$ in the compound of formula XV is a —$COOR^{13}$ this group can be converted to the compound of formula XVI where $R^{10}$ is formyl by reduction. Any conventional reducing agents such as diisobutyl aluminum hydride, which are utilized to reduce esters to their corresponding aldehydes, can be utilized in this conversion. If it is desired to prepare the compound of formula XVI where $R^{10}$ is formyl protected by formation of an acetal, the formyl group can be converted to an acetal by conventional means.

If desired, the compound of formula XV where $R^{20}$ is —$CH_2R^{19}$ and $R^{19}$ taken together with $R^8$ forms lower alkylidenedioxy can be converted to the compound for formula XVI where $R^{10}$ is —$CH_2Y$ and Y is a leaving group and $R^6$ is a hydrolyzable ether group. In this regard, the alkylidenedioxy group in the compound of forms XV is first hydrolyzed to form the corresponding compound of formula XV where $R^{20}$ is —$CH_2OH$ and $R^8$ is —OH. This hydrolyzable product is then treated by conventional means so that the —OH group in the $CH_2OH$ substituent represented by $R^{20}$ is converted to a leaving group such as mesyloxy or tosyloxy. The formation of a leaving group occurs at the —CH₂OH substituent and not at the —OH substituent represented by R⁸. The —OH substituent represented by R⁸ can thereafter be etherified by a conventional mean to form a hydrolyzable ether preferably a benzyl ether or tri(-lower alkyl) silyl ether.

The compound of formula XVI, which includes the compound XV when R⁸ and R¹⁹ form lower alkylidenedioxy, can be converted to the compound of formula II by treating the compound of formula XVI with a halogenating agent such as organic or inorganic hypohalite preferably calcium hypohalite, sodium hypohalite or t-butylhypohalite in the presence of a tertiary amine base. Any conventional tertiary amine base can be utilized in carrying out this reaction. Among the preferred tertiary amine bases are the tri-lower alkyl amines and the cyclic tertiary amines. Among the preferred cyclic tertiary amines included N-lower alkylpyrrolidine, N-lower alkylpiperidine, N,N-di-lower alkylaniline, pyridine, etc. In carrying out this reaction an inert organic solvent can be utilized. On the other hand, the amine base can act as the solvent medium. If it is desired to utilize a solvent generally aprotic solvents, such as halogenated hydrocarbons, ethers and dimethylformamide are preferred. In carrying out this halogenation, temperature and pressure are not critical and this reaction can be carried out at room temperature and atmospheric pressure, with temperatures of —40° C. to 30° C. being generally preferred.

The compounds of formula II-B can be prepared from compound of formula XVI via intermediates of the formula

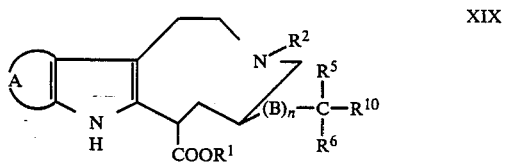

XIX wherein n, R¹, R², R⁵, R⁶, A, B, and R¹⁰ are as above with the proviso that where R⁶ is a hydrolyzable ether group, and R¹⁰ is —CH₂Y, Y is a leaving group.

The compound of formula XVI can be converted to the intermediate of the formula XIX by reduction with an alkali metal borohydride, preferably sodium borohydride in an inorganic or organic acid. This reaction can be carried out in the same manner described hereinbefore in converting the compound of formula III to the compound of formula V except that temperature of at least 40° C., preferably 70° C. to 100° C., are generally utilized for this conversion.

The compound of formula XIX can be converted to the compound of formula II-B by chlorination with a hypohalite, such as t-butyl hypochlorite, sodium hypochlorite or calcium hypochlorite in the presence of a tertiary amine. This reaction is carried out in the same manner as described hereinbefore in connection with the formation of the compound of formula II.

The compounds of formula I wherein the vindoline ring contains a methyl group at R₅, i.e. compounds of the vinblastine type, can be converted to the corresponding compounds where R₅ is CHO, i.e. compounds of the vincristine type by oxidation procedures well known in the art.

The following examples are illustrative but not limitative of the claimed invention. In the example, the ether is diethyl ether and Celite is diatomaceous earth. HPLC in the examples designates high pressure liquid chromatography.

EXAMPLE 1

Methyl 3-Benzyl-1,2,3,3a,4,5-hexahydro-4(3-hydroxypropyl)-7H-pyrrolo(2,3-d)carbazole-6-carboxylate To methyl 1,2,3,4,5,6-hexahydroazepino(4,5-b)indole-5-carboxylate (5.0 g, 20 mmol) stirring in methanol (25 mL) was added enough methanol saturated with HCl to turn moist universal pH paper red. The methanol was evaporated at reduced pressure and to the residue was added H₂O (50 mL) and 2-hydroxytetrahydropyran (2.2 g, 22 mmol) and the mixture was allowed to stir at 20° C. overnight. TLC (SiO₂, 7.5% methanol/CH₂Cl₂) of the mixture showed the formation of two products which were methyl 1,2,4,6-tetrahydro-11-β(4-hydroxybutyl)-3,10b-methanoazepino (4,5-b)indole-5-carboxylate and methyl 1,2,4,6-tetrahydro-11-α(4-hydroxybutyl)-3,10b-methanoazepino (4,5-b)indole-5-carboxylate (Rf 0.68 and 0.76, CAS, blue). The reaction mixture was basified (NH₄OH), 10% (aq) and extracted three times with CH₂Cl₂. The organic extracts were dried (Na₂SO₄) and concentrated to a residue, which was immediately dissolved in THF (100 mL). To the THF solution was added benzyl bromide (2.5 mL, 21 mmol) and then the solution was heated to reflux and monitored by TLC until conversion to the mixture of 3-benzyl 1,2,4,6-tetrahydro-11-β(4-hydroxybutyl)-5-methoxycarbonyl-3,10b-methanoazepino (4,5-b)indolium bromide and 3-benzyl-1,2,4,6-tetrahydro-11-α(4'-hydroxybutyl)-5-methoxycarbonyl-3,10b-methanoazepino (4,5-b)indolium bromide (about 2 h) was completed. At this point the THF was evaporated and replaced with methanol (100 mL) and diisopropyl ethyl amine (5.3 mL). Reflux was restarted until TLC showed complete disappearance of the above mixture of compounds. The methanol was evaporated and the residue chromatographed (SiO₂, 5% methanol/CH₂Cl₂) to yield 5.7 g (67%) of methyl 3-benzyl-1,2,3,3a,4,5-hexahydro-4(3-hydroxy-propyl)-7H-pyrrolo(2,3-d)carbazole-6-carboxylate as a gum;TLC (SiO₂, 7.5% methanol/CH₂Cl₂) Rf 0.86 CAS, blue).

EXAMPLE 2

Methyl 3-Benzyl-1,2,3,3a,4,5-hexahydro-4(3-p.toluenesulenefonyloxypropyl)-7H-pyrrolo(2,3-d) carbazole-6-carboxylate Methyl 3-benzyl-1,2,3,3a,4,5-hexahydro-4(3-hydroxypropyl)-7H-pyrrolo(2,3-d)carbazole-6-carboxylate (1.0 g, 2.4 mmol) and p-toluenesulfonyl chloride (0.55 g, 2.9 mmol) were stirred in pyridine (4 mL) under a nitrogen atmosphere at 20° C. overnight. The mixture, which had developed a precipitate, was diluted with CH₂Cl₂, washed with 10% NH₄OH and brine, dried (Na₂SO₄) and taken to dryness first at aspirator pressure and then high vacuum in order to avoid excess heating of the product. The residue was dissolved in methanol and allowed to crystallize overnight in the freezer; yield methyl 3-benzyl-1,2,3,3a,4,5-hexahydro-4(3-p.toluenesulfonyloxypropyl)-7H-pyrrolo(2,3-d)carbazole-6-carboxylate 0.59 g (40%). An analytical sample was recrystallized from methanol, mp 158°–159° C. TLC (SiO₂, 7.5% methanol/CH₂Cl₂) Rf 0.91 (CAS, blue).

EXAMPLE 3

Methyl 3-Benzyl-1,2,3,3a,4,5-hexahydro-4(3-p.toluenesulenefonyloxypropyl)-7H-pyrrolo(2,3-d)carbazole-6-carboxylate A solution of methyl 3-benzyl-1,2,3,3a,4,5-hexahydro-4(3-hydroxypropyl)-7H-pyrrolo(2,3-d)carbazole-6-carboxylate (1.95 g, 4.66 mmol), and two small crystals of 4-dimethylaminopyridine in 8 mL of anhydrous pyridine was cooled to 0° C. and 0.890 g (4.70 mmol) of p-toluenesulfonyl chloride added. The clear red solution was stirred at 15° C. for 15 h, resulting in formation of a precipitate. The mixture was then poured into 20 mL of water and extracted with 25 mL of dichloromethane. The organic phase was washed with water, aqueous ammonium hydroxide, and brine and dried ($Na_2SO_4$). Concentration under vacuum and azeotropic removal of pyridine with toluene at 50° C. at 15 mm, followed by drying under high vacuum, gave a residue which was column chromatographed on silica, eluting with 4:6 ethyl acetate:hexane. The product methyl 3-benzyl-1,2,3,3a,4,5-hexahydro-4(3-p.toluenesulfonyloxypropyl)-7H-pyrrolo(2,3-d)carbazole-6-carboxylate (2.00 g, 75% yield) matched the previously characterized sample, prepared in Example 2 in mp and spectroscopic data.

EXAMPLE 4

5,7-Priority Anti-reflective (PARF) Methyl 3-Benzyl-1,2,3,4,5,6,7,8-octahydro-5(3-ptoluenesulfonyloxypropyl)azonino (6,7-b)indole-7-(15-vindolinyl)-7-carboxylate A solution of methyl 3-benzyl-1,2,3,3a,4,5-hexahydro-4 (3-p.toluenesulfonyloxypropyl)-7H-pyrrolo(2,3-d)carbazole-6-carboxylate (0.740 g, 1.30 mmol) in 10 mL of dichloromethane and 0.18 mL (1.3 mmol) of triethylamine was cooled to 0° C. Dropwise addition of 0.200 mL (1.69 mmol) of t butylhypochlorite and stirring for 10 min. gave a solution which, by TLC was free of starting compound (CAS, blue) and which contained a new less polar compound (CAS, brown). The reaction mixture was washed with 2×10 mL of water, 10 mL of brine and dried ($Na_2SO_4$). Concentration under vacuum gave 0.800 g (1.30 mmol) of methyl 3-benzyl-6-chloro 1,2,3,3a,4,5-hexahydro-4(3-p-toluenesulfonyloxypropyl)-pyrrolo(2,3-d)carbazole-6-carboxylate as a white foam.

To a solution of 0.800 g of methyl 3-benzyl-6-chloro 1,2,3,3a,4,5-hexahydro-4(3-p.toluenesulfonyloxypropyl)pyrrolo(2,3-d) carbazole-6-carboxylate and vindoline 1.5 hydrochloride (0.456 g, 0.895 mmol) in 15 mL of dry acetone was added a solution of 0.80 g (4.0 mmol) of $AgBF_4$ in 15 mL of dry acetone at room temperature. After 5 min. the heterogeneous gray reaction mixture contained no starting material. Addition of 10 mL of conc. ammonium hydroxide, 10 mL of water and 10 mL of brine, extraction with 3×20 mL of dichloromethane, washing of the extracts with brine, drying ($Na_2SO_4$) and concentration gave 1.20 g of the 6S and 6R isomers of 4,6-priority anti-reflective (PARF) methyl 3-benzyl-1,2,3,3a,4,5-hexahydro-4-(3-p.toluenesulfonyloxypropyl)-6-(15-vindolinyl)pyrrolo (2,3-d)carbazole-6-carboxylate.

The 6S and 6R isomeric mixture of 4,6-priority anti-reflective (PARF) methyl 3-benzyl-1,2,3,3a,4,5-hexahydro-4-(3-p.toluenesulfonyloxy-propyl)-6-(15-vindolinyl)pyrrolo-(2,3-d)carbazole-carboxylate was dissolved in 15 mL of acetic acid and, with stirring at room temperature, 0.54 g (10 mmol) of sodium borohydride was added in six portions. After the final addition the reaction mixture was stirred for 10 min. and then poured onto ice. Adjustment of the PH to 9–10 with conc. ammonium hydroxide was followed by extraction with 60 mL of dichloromethane. The extract was washed with water (3×25 mL), brine (25 mL), dried ($Na_2SO_4$) and concentrated to 1.10 g of a yellow solid. Column chromatography on silica, eluting with ethyl acetate, gave 0.83 g (91% yield based on 1 mmol of vindoline) of the mixture of 7S and 7R isomers of 5,7-priority anti-reflective (PARF) methyl 3-benzyl-1,2,3,4,5,6,7,8-octahydro-5(3-p.toluenesulfonyloxypropyl)azonino (6,7-b)indole-7-(15-vindolinyl)-7-carboxylate as a white solid, $R_f$ 0.25 ($SiO_2$, ethyl acetate, CAS brown). These diastereoisomers showed slight separation on TLC using methanol-dichloromethane as solvent.

A better separation of the 7S and 7R isomers was obtained with 1:1 hexane:acetone on silica, showing $R_f$ 0.37 for the 7S compound and $R_f$ 0.27 for the 7R compound. Thus, separation of 0.830 g of the mixture on a 2 mm centrifugal chromatography plate gave 0.374 g of the 7S compound and 0.332 g of the 7R compound.

EXAMPLE 5

Methyl 3-Benzyl-1,2,3,4,5,6,7,8-octahydro-5β(3-p.toluenesulfonyloxypropyl) azonino (6.7-b) indole-7α and β-carboxylates Methyl 3-benzyl-1,2,3,3a,4,5-hexahydro-4(3-p-toluenesulfonyloxypropyl)-7H-pyrrolo(2,3-d)carbazole-6-carboxylate (0.10 g, 0.17 mmol) was dissolved in acetic acid 1 mL) and heated in a 90° C. oil bath. Sodium borohydride (0.040 g, 1.1 mmol) was added quickly in portions and the reaction was quenched by pouring onto ice. The aqueous phase was basified with $NH_4OH$ (10% aq) and concentrated to a residue, which was chromatographed ($SiO_2$, 2% methanol/$CH_2Cl_2$) to yield the 7% isomer of methyl 3-benzyl-1,2,3,4,5,6,7,8-octahydro-5β(3-p.toluenesulfonyloxypropyl) (6,7-b) indole-7-carboxylate (0.055 g, 55%) and the 7β isomer of methyl-3-benzyl-1,2,3,4,5,6,7,8-octahydro-5β(3-p.toluenesulfonyloxypropyl) azonino (6,7-b) indole-7-carboxylate (0.015 g, 15%) as amorphous solids. These compounds tended to undergo, on standing, cyclization to the internal quaternary salt.

Physical data for the 7α isomer of methyl 3-benzyl-1,2,3,4,5,6,7,8-octahydro-5β(3-p.toluenesulfonyloxypropyl) azonino (6,7-b) indole-7-carboxylate: TLC ($SiO_2$, 1.5% methanol/$CH_2Cl_2$) $R_f$ 0.74 (CAS, violet). Physical data for the 7β isomer of methyl 3-benzyl-1,2,3,4,5,6,7,8-octahydro-5β(3-p.toluenesulfonyloxypropyl) azonino (6,7-b) indole-7-carboxylate: TLC ($SiO_2$, 1.5% methanol/$CH_2Cl_2$) $R_f$ 0.47 (CAS, violet).

EXAMPLE 6

5,7-priority Anti-reflective (PARF) Methyl 3-Benzyl-1,2,3,4,5,6,7,8-octahydro-5(3-p.toluenesulfonyloxypropyl)azonino (6,7-b)indole-7-(15-vindolinyl)-7-carboxylate A solution of the epimeric mixture of methyl 3-benzyl-1,2,3,4,5,6,7,8-octahydro-5β(3-p.toluenesulfonyloxypropyl)azonino(6,7-b) indole-7α and β-carboxylates (0.574 g, 1.00 mmol) and 0.18 mL (1.3 mmol) triethylamine in 10 mL of dichloromethane was cooled to 0° C. Dropwise addition of 0.15 mL (1.3 mmol) of t-butylhypochlorite resulted in a clear yellow solution, which, after 15 min at 0°-5° C., showed complete reaction of the starting epimers (CAS blue) and formation of the slightly less polar (TLC $R_f$ 0.8, 5% methanol in dichloromethane) methyl 3-benzyl-12b-chloro-1,2,3,4,5,6,8,12b-octahydro-5(3-p.toluenesulfonyloxy-propyl)azonino (6,7-b)-indole-7-carboxylate (CAS orange). The reaction mixture was diluted with 20 mL of dichloromethane, washed with water (2×50 mL) and brine (1×20 mL), dried (MgSO$_4$) and concentrated under vacuum to 0.61 g (100%) of an orange foam. This material was used directly in the subsequent coupling reaction with vindoline.

To a solution of the above indoline, i.e., methyl 3-benzyl-12b-chloro-1,2,3,4,5,6,8,12b-octahydro-5(3-p.toluenesulfonyloxypropyl)azonino (6,7-b)-indole-7-carboxylate (0.61 g, 1.0 mmol) and vindoline 1.5 hydrochloride (0.365 g, 0.715 mmol) in 7 mL of dry methanol was added 5 mL of methanolic HCl (formed by solution of 0.3 mL of acetyl chloride in 10 mL of methanol). The clear burgundy red reaction mixture was stirred at room temperature for 15 h. The mixture was then concentrated under vacuum, basified with ammonium hydroxide and extracted with 30 mL of dichloromethane. The extract was washed with 2×50 mL of water, 1×20 mL of brine, dried (MgSO$_4$) and concentrated under vacuum to 0.85 g of a gummy residue. Chromatography on silica gel, eluting with ethyl acetate, gave 0.40 g (48%) of the 5,7-priority anti-reflective (PARF) methyl 3-benzyl-1,2,3,4,5,6,7,8-octahydro-5(3-p.toluenesulfonyloxypropyl)azonino (6,7-b)indole-7-(15-vindolinyl)-7-carboxylate as a pale yellow solid. The product was identical by TLC, NMR and mass spectra to the above characterized product obtained in Example 4.

EXAMPLE 7

4'-Deethyl-4'-deoxyvinblastine (2'S.18'S) and 4'-Deethyl-4'-deoxyvinblastine (2'R,18'R)

(a) The mixture of diastereoisomers 5,7-priority anti-reflective (PARF) methyl 3-benzyl-1,2,3,4,5,6,7,8-octahydro- 5(3-p.toluenesulfonyloxypropyl)azonino (6,7-b)indole-7-(15-vindolinyl)-7-carboxylate (0.258 g, 0.250 mmol) was dissolved in 2.5 mL of dry toluene and heated at reflux, with stirring for 1.5 h. At that point the quaternary salts 6'-benzyl-4'-deethyl-4'-deoxyvinblastinonium tosylate (2'S,18'S) and 6'-benzyl-4'-deethyl-4'-deoxyvinblastinonium tosylate (2'R, 18'R), both in the form of their 1'-equatorial piperidine ring conformational isomer, had precipitated as a brown gum and TLC indicated complete reaction of the starting material. The solvent was removed under vacuum and the residual solid 6'-benzyl-4'-deethyl-4'-deoxyvinblastinonium tosylate (2'S,18'S) and 6'-benzyl-4'-deethyl-4'-deoxyvinblastinonium tosylate (2'R, 18'R) (0.258 g, 100%) with $R_f$ (SiO$_2$, 95:5 CH$_2$Cl$_2$: methanol, CAS pink) 0.05 was used directly in the following debenzylation.

A solution of 0.206 g (0.200 mmol) of the above solid in 5 mL of dry methanol was stirred with 20 mg of 10% palladium on charcoal under a hydrogen atmosphere at −5° to 0° C. for 55 min. when 4.5 mL (0.20 mmol) of hydrogen had been consumed. Filtration through Celite, concentration at 20° C. and partitioning of the residue between 30 mL of dichloromethane and 10% aq. ammonium hydroxide, followed by washing of the organic extracts with water and brine gave, on concentration, 150 mg (99%) of the two diastereoisomeric products 4'-deethyl-4'-deoxyvinblastine (2'S,18'S) and 4'-deethyl-4'-deoxyvinblastine (2'R,18'R) both in form of a mixture their 1'-equatorial and 1'-axial piperidine ring conformational isomers. These two products, in 5 mL of toluene, were heated at reflux for 2 h. TLC then showed formation of the two diastereoisomeric products 4'-deethyl-4'-deoxyvinblastine (2'S,18'S) and 4'-deethyl-4'-deoxyvinblastine (2'R,18'R) both with the 1' axially substituted piperidine ring conformation. TLC (SiO$_2$: 10% methanol in CH$_2$Cl$_2$, CAS brown) 0.16 and 0.35. Concentration and centrifugal chromatography on a 2 mm SiO$_2$ plate, eluting with 5% methanol in CH$_2$Cl$_2$,gave 32 mg of 4'-deethyl-4'-deoxyvinblastine (2'S, 18'S) ($R_f$ 0.16), and 35 mg of its (2'R, 18'R) enantiomeric diastereoisomer ($R_f$ 0.35). Yield 47% for each diastereoisomer.

Alternatively, the separate 7S and 7R diastereoisomers of methyl 3-benzyl-1,2,3,4,5,6,7,8-octahydro-5(3-p.toluenesulfonyloxypropyl) azonino (6,7-b) indole-7-(15-vindolinyl)-7-carboxylate, when subjected to the same reaction procedure of heating in toluene, followed by hydrogenolysis, gave respectively, prior to the final heating in toluene, the separate 2'S,18'S and the 2'R,18'R diastereoisomers of 4'-deethyl-4'-deoxyvinblastine, each as a mixture of the 1'-equatorial and 1'-axial piperidine ring conformational isomers. The 2'S,18S',1' equatorial compound had an HPLC retention of 37 min on a 250×4.6 mm C-18 reverse phase column with 1% triethylamine in 70:30 methanol:water at a 0.85 mL/min flow rate.

The above 1'-equatorial compound was conformationally inverted to the 2'S,18'S,1' axial 4'-deethyl-4'-deoxyvinblastine by heating in toluene at 95° C. This product had an HPLC retention of 15 min on the same Column at the same flow rate. The 2'R,18'R,1' equatorial compound had HPLC retention of 39 min on a 250×4.6 mm C-18 reverse phase column with 1% triethylamine in 70:30 methanol:water at a 0.85 mL min flow rate. It was conformationally inverted to the 2'R,18'R,1' axial 4'-deethyl-4'-deoxyvinblastine by heating in toluene at 100° C. This product had an HPLC retention of 13 min on the same column at the same flow rate.

EXAMPLE 8

4'-Deethyl-4'-deoxyvinblastine (2'S,18'S) and 4'-deethyl-4'-deoxyvinblastine (2'R, 18'R)

The quaternary salts 6'-benzyl-4'-deethyl-4'-deoxyvinblastinonium tosylate (2'S,18'S) and 6'-benzyl-4'-deethyl-4' -deoxyvinblastinonium tosylate (2'R, 18'R) were dissolved in methanol (5 mL) and the solution was purged with nitrogen. Palladium catalyst (10% pd/C, 0.10 g) was added, the flask fitted with a reflux condenser and heated in a 90° C. oil bath. An excess of sodium borohydride (ca. 0.3 g) was added through the top of the condenser as rapidly as possible, so that the vigorous reaction could be contained. TLC's were taken throughout this procedure to qualitatively determine if any starting material remained. The addition of the borohydride reagent took about 5 min. A short reaction time was necessary because a less polar side product seemed to form on longer reaction times. The hot solution was filtered and washed with hot methanol (ca. 50 mL) followed by CH$_2$Cl$_2$ (ca. 10 mL). The solution was partially concentrated and NH$_4$OH (10% aq) was added. The aqueous solution was extracted with $CH_2Cl_2$, the organic extracts were dried ($Na_2SO_4$) and concentrated to a residue which was a 1:1 parts by weight mixture of the diastereoisomers 4′-deethyl-4′-deoxyvinblastine (2′S,18′S) and 4′-deethyl-4′-deoxyvinblastine (2′R,18′R). Yield 0.13 g (70%). Physical data for the 2′R 18′R epimer: TLC ($SiO_2$; 10% methanol/$CH_2Cl_2$) $R_f$ 0.37 (CAS, brown). Physical data for the 2′S, 18′S epimer: TLC ($SiO_2$, 10% methanol/$CH_2Cl_2$) $R_f$ 0.23 (CAS, brown).

EXAMPLE 9

4′-Deethyl-4′-deoxyvinblastine and its 2′R,18′R epimer

A solution of 5,7-priority anti-reflective (PARF) methyl 3-benzyl-1,2,3,4,5,6,7,8-octahydro-5β-(3-p.toluene-sulfonyloxypropyl)azonino(6,7-b) indole-7-(15-vindolinyl)-7-carboxylate(7α and 7β) (0.100 g, 0.092 mmol), in 10 mL of acetic acid and 0.02 g of 10% Pd on charcoal was stirred under a hydrogen atmosphere for 3 h. The reaction mixture was then filtered through Celite, made basic with ammonium hydroxide and extracted with 20 mL of dichloromethane. The extract was washed with 2×20 mL of water, 1×20 mL of brine, dried ($MgSO_4$) and concentrated under vacuum to 0.060 g of a yellow solid. TLC indicated that this product was 4′-deethyl-4′-deoxyvinblastine and its 2′R 18′R epimer with the "natural type" piperidine ring conformation and that none of the C16′-C14′ PREF diastereoisomers (epimeric with the products at C16′) were formed.

Chromatographic separation of the two products i.e. deethyl-4-deoxyvinblastine (2′S,18′S) and deethyl-4-deoxyvinblastine (2′R,18′R) as described in Example 7, and comparison of their NMR and mass spectra with those of the products obtained from conformational inversion of the piperidine ring of the "unnatural" type piperidine conforms i.e. 1′-equatorial piperidine ring conformational isomer of 2′R,18′R and 2′S, 18′S, 4′-deethyl-4′deoxyvinblastine, showed complete matching of spectra.

EXAMPLE 10

Methyl 2-Ethyl-5-hydroxyvalerate

A solution of 30.0 g (0.234 mmol) of 2-ethylvalerolactone in 150 mL of dry methanol and 0.5 mL of conc. sulfuric acid was stored under argon for 17 h at 20° C. Then 10.0 g of potassium carbonate was added and the mixture stirred for 20 min. After filtration, and concentration at 40° C. under vacuum, the residue was dissolved in 100 mL of ether. The solution was washed with 200 mL of satd. sodium carbonate, 100 mL of satd. brine, dried over $MgSO_4$, filtered, concentrated and the residue distilled to give 32.1 g (86%) of methyl 2-ethyl-5-hydroxyvalerate, bp 58°-60° C. (0.5 mm Hg).

EXAMPLE 11

Methyl 2-Ethyl-5-Oxopentanoate

To 50.46 g (0.234 mmol) of pyridinium chlorochromate, under argon, was added 100 mL of dichloromethane followed, with rapid stirring, by 25.0 g (0.156 mmol) of methyl 2-ethyl-5-hydroxypentanoate in 20 mL of dichloromethane. After stirring at 20° C. for 2.5 h, 15 g of silica gel was added followed by 200 mL of ether. Filtration through a 3.5×40 cm silica gel column (60–200 mesh), eluting ether and concentration at 40° C. under vacuum gave an oil, which was redissolved in 100 mL of dichloromethane. Washing with 3×100 mL of cold 1N HCl, 3×100 mL of satd. $NaHCO_3$, drying over $MgSO_4$, filtration, concentration at 40° C. and distillation gave methyl 2-ethyl-5-oxopentanoate 14.64 g (59%) product, b.p 104°–105° C. (16 mm Hg).

EXAMPLE 12

Racemic Methyl 1,2,4,6-Tetrahydro-11-(1-ethyl-4-methoxy-4-oxobutyl)-3,10b-methanoazepino (4,5-b)indole-5-carboxylate To a solution of 6.00 g (24.6 mmol) of methyl 1,2,3,4,5,6-hexahydroazepino-[4,5-b] indole-5-carboxylate in 50 mL of dry methanol, under argon, was added 4.00 g (25.3 mmol) of methyl 2-ethyl-5-oxopentanoate. After 12 h at 20° C. the mixture was concentrated under vacuum at 40° C. and the residue dissolved in dichloromethane. The solution was adsorbed on 20 g of $SiO_2$, which was then placed on a 4×15 cm dry column of $SiO_2$. Elution with ethyl acetate, concentration, solution of the concentrated eluate in 100 mL of dichloromethane, drying over $MgSO_4$, filtration, and concentration gave an oily product from which two successive 100 mL portions of toluene were distilled at 40° C. under vacuum. Drying at 20° C. (0.05 mm) provided as a foam 7.70 g (82%) racemic methyl 1,2,4,6-tetrahydro-11-(1-ethyl-4-methoxy-4-oxobutyl)-3,10b-methanoazepino (4,5-b)indole-5-carboxylate. This product had UV (ethanol $\lambda_{max}$ 228, 303, 330 nm absorption maxima.

EXAMPLE 13

4,2′-PREF and 4,2′-PARF Methyl 3-Benzyl-1,2,3,3a,4,5hexahydro-4[2-(hydroxymethyl)-butyl]-7H-pyrrolo (2,3-d) carbazole-6-carboxylate A solution of 6.182 g (16.08 mmol) of the methyl 1,2,4,6-tetrahydro-11-(1-ethyl-4-methoxy-4-oxobutyl)-3,10b-methanoazepino-(4,5-b)indole-5-carboxylate and 2.750 g (16.08 mmol) of benzyl bromide in 100 mL of anhydrous ether was stirred for 48 h at 20° C. under argon. Filtration, washing of the solids with 3×100 mL of ether and drying at 15 mm and 0.01 mm pressure gave 8.422 g (94%) of the quaternary salt 3-benzyl 1,2,4,6-tetrahydro-11-(1-ethyl-4-methoxy-4-oxobutyl)-5-methoxycarbonyl-3,10b-methanazepino (4,5-b)indolium bromide.

A solution of 4.000 g (7.201 mmol) of the above quaternary salt in 40 mL of methanol and 1.100 g (10.80 mmol) of triethylamine was heated at reflux under argon for 5 h. At 40° C. (15 mm) the solution was then concentrated to a residual orange gum and the latter dissolved in 50 mL of dichloromethane. Washing with iced 15% ammonium hydroxide and satd. brine, with back extraction of the latter with 50 mL of dichloromethane, drying of the combined organic solutions ($MgSO_4$), filtration and concentration at 40° C. (15 mm and 0.01 mm) gave a foam, which was chromatographed on a 3×15 cm $SiO_2$ column, eluting with 1:4 ethyl acetate: pentane. The diastereoisomeric mixture of esters 4,2′-PREF and 4,2′-PARF-Methyl 3-benzyl-1,2,3,3a,4,5-hexahydro-4-[2-(methoxycarbonyl)butyl]-7H-pyrrolo-(2,3-d)carbazole-6-carboxylate (2.737 g, 80% yield) showed almost no separation on TLC ($SiO_2$), $R_f$0.61 (2:1 ether-hexane); $R_f$0.43 (2% methanol in dichloromethane); $R_f$0.41 (1:4 ethyl acetate:pentane). This epimeric mixture could be separated by HPLC on a 22.1 mm×50 cm 10 μm Silica column with ether:hexane 1:3 at flow rate of 8.0 mL/min, giving the PREF isomer with $R_f$ 50 min and the PARF isomer with $R_f$ 57 min in a 1.47:1.00 ratio.

A solution of 2.147 g 4.526 mmol) of the diastereoisomeric mixture of 4,2'-PREF and 4,2'-PARF-Methyl 3-benzyl-1,2,3,3a,4,5-hexahydro-4-[2-(methoxycarbonyl)-butyl]-7H-pyrrolo(2,3-d)carbazole-6-carboxylate in 20 mL of dry tetrahydrofuran, under an argon atmosphere, was cooled to 0° C. With rapid stirring 5.40 mL of a 1.0 M solution of lithium aluminum hydride in tetrahydrofuran (5.43 mmol) was added dropwise over 10 min. After stirring at 0° C. for further 20 min., the reaction mixture was poured into 100 mL of iced 30% ammonium hydroxide and extracted with 3×50 mL of dichloromethane. The combined extracts were washed with 100 mL of cold satd. brine, dried (MgSO4) filtered and concentrated at 40° C. (15 mm and 0.01 mm) to 1.744 g (86% yield) of 4,2'-PREF and 4,2'-PARF methyl 3-benzyl-1,2,3,3a,4,5-hexahydro-4-[2-(hydroxymethyl)butyl]-7H-pyrrolo(2,3-d)carbazole-6-carboxylate as a foam. TLC (SiO2, ether) $R_f$ 0.50 (PREF isomer) and 0.56 (PARF isomer). A 0.50 g portion of this product was subjected to centrifugal chromatography on a 2 mm SiO2 plate. application in 5 mL of dichloromethane was followed by elution with 4:1 ether:hexane at 2.2 mL/min. and collection of 1 min. fractions. Fractions 5–30 and 52–90 contained the two nearly pure diastereoisomic PARF and PREF isomers.

EXAMPLE 14

4,2'PREF- and 4,2'PARF Methyl 3-Benzyl-1,2,3,3a,4,5-hexahydro-4[2-(p.toluenesulfonyloxymethyl)-butyl]-7H-pyrrolo(2,3-d) carbazole-6-carboxylate Under an argon atmosphere 0.980 g (2.19 mmol) of the 4,2' PREF and 4,2' PARF methyl 3-benzyl-1,2,3,3a,4,5-hexahydro-4[2-(hydroxymethyl)-butyl]-7H-pyrrolo(2,3-d) carbazole-6-carboxylate was combined with 0.460 g (2.41 mmol) of p-toluenesulfonyl chloride and 5 mg of 4-dimethylamino pyridine. At 0° C. 10 mL of dry pyridine was added and the reaction mixture stirred at 0° C. for 4 h and at 4° C. for 24 h. The red solution was then poured into 50 mL of cold 1N ammonium hydroxide and extracted with 3×50 mL of dichloromethane. The combined extracts were washed with 100 mL of cold satd. brine, dried (MgSO4), filtered and concentrated at 40° C. (15 mm). Two 100 mL portions of toluene were then added and distilled at 40° C. under vacuum, providing 0.991 g (75% yield) of the 4,2' PREF- and 4,2' PARF methyl 3-benzyl-1,2,3,3a,4,5-hexahydro-4[2-(p.toluenesulfonyloxypropyl)-7H-pyrrolo(2,3-d) carbazole-6-carboxylate. TLC (SiO2) $R_f$ 3.0 and 3.7, 1:4 ethyl acetate:pentane; $R_f$ 4.6 and 5.1, 5% methanol in dichloromethane.

The epimeric mixture of tosylates could be separated by centrifugal chromatography on a 4 mm SiO2 plate, with application in 10 mL of dichloromethane and elution with ethyl acetate:pentane (1:5). At 2.2 mL/min and with collection of 1 min fractions, the PARF isomer was obtained in fractions 6–26 and the 4,2' PREF isomer in fractions 99–170. Rechromatography of central fractions (5×) gave final 0.420 g combined PARF isomer and 0.391 g combined PERF isomer (total 0.811 g, 61% yield).

Alternatively, separation of the diastereoisomic tosylates was accomplished by preparative high pressure liquid chromatography. For this, the crude reaction product was first passed through a 3×10 cm SiO2 column, eluting with ethyl acetate:pentane (1:2). The concentrated eluates (200 mg) were then subjected to HPLC on a 22.1 mm ×50 cm 10 μm, Silica column, with ethyl acetate:pentane 1:4, 20 mL/min. Collecting 24 mL 12–17 112 mg of the respective diastereoisomers (94% recovery).

EXAMPLE 15

7S and 7R isomers of 5,7 PARF and 5,2' PARF Methyl 3-Benzyl 1,2,3,4,5,6,7,8-octahydro-5[2-(p.toluenesulfonyloxymethyl)-butyl]azonino (6,7-b) indole 7-(15-vindolinyl)-7-carboxylate A solution of 6.36 g (1.06 mmol) of the 4,2' PARF-methyl 3-benzyl-1,2,3,3a,4,5-hexahydro-4[2-(p.toluenesulfonyloxymethyl)-butyl]-7H-pyrrolo(2,3-d)-carbazole-6-carboxylate in 10 mL of dichloromethane and 0.118 g (0.162 μL, 1.16 mmol) of triethylamine was cooled to 0° C. under argon. With vigorous stirring 135 μL (0.126 g, 1.16 mmol) of tert. butyl hypochlorite was added. After 20 min at 0° C. the yellow reaction mixture was poured into 20 mL of iced water and the mixture extracted with 3×10 mL of dichloromethane. The combined extracts were dried (MgSO4), filtered and concentrated at 20° C. at 15 mm and subsequently at 0.05 mm pressure to a tan foam which was methyl 3-benzyl-6-chloro 1,2,3,3a,4,5-hexahydro 4-[2-(p.toluenesulfonyloxy-methyl)-butyl]-pyrrolo(2,3-d) carbazole-6-carboxylate, 0.672 g (100%). This chloroindolenine (0.636 g, 1.00 mmol) and 0.374 g (0.735 mmol) of vindoline 1.5 hydrochloride were placed under argon and 10 mL of dry acetone was added. After stirring for 5 min, 0.618 g (3.18 mmol) of silver tetrafluoroborate in 4 mL of dry acetone was added in one portion, with shielding from light. After stirring in the dark for 20 min the brown suspension was poured into 50 mL of 10% ammonium hydroxide, saturated with sodium chloride, and the mixture was extracted with 3×25 mL of dichloromethane. The combined dried (MgSO4) extracts were filtered and concentrated at 40° C., 15 mm to a brown glass. TLC (SiO2, ethyl acetate) demonstrated the two imines 4,6-PARF and 4,6-PREF methyl 3-benzyl-1,2,3,3a,4,5-hexahydro-4-[2-(p.toluenesulfonyloxymethyl)butyl]-6-(15-vindolinyl)-pyrrolo (2,3-d) carbazole-6-carboxylate ($R_f$ 0.13 and 0.46) and the absence of vindoline ($R_f$ 0.32). This imine mixture was dissolved in 25 mL of acetic acid and 0.571 g (10.6 mmol) of potassium borohydride was added in portions over 15 min, with rapid stirring. The reaction mixture was then poured into cold ammonium hydroxide solution and extracted with 3×50 mL of dichloromethane. The combined extracts were dried (MgSO4) filtered and concentrated at 40° C. at 15 mm and subsequently at 0.05 mm Hg to give 0.660 g (85% yield based on vindoline used) of the two amines, i.e. 7R and 7S 5,7 PARF -5,2' PARF methyl 3-benzyl-1,2,3,4,5,6,7,8-octahydro-5-[2-(p.toluenesulfonyloxymethyl)-butyl]-azonino (6,7-b)indole-7-(15-vindolinyl)-7-carboxylate as a tan foam. TLC (SiO2, ethyl acetate) $R_f$ 0.37 and 0.49 (CAS grey-purple). Centrifugal chromatography on a 4 mm SiO2 plate, with application of the mixture in 10 mL of dichloromethane, followed by elution with 10 mL of dichloromethane and then 80% ethyl acetate in pentane at 2.1 mL/min and collection of fractions every minute gave the separated diastereoisomers. In fractions 3 to 30, the 7S isomer of 5,7 PARF and 5,2' PARF methyl 3-benzyl-1,2,3,4,5,6,7,8-octahydro-5[2-(p.toluenesulfonyloxymethyl)butyl]-azonino(6,7-b)indole-7-(15-vindolinyl)-7-carboxylate and in fractions 52 to 90 the corresponding 7R isomer. Rechromatography of the fractions 31–51 provided additional separated compounds, for a combined 0.300 g of the 7S isomer and 0.271 g of the 7R isomer (66% total yield based on vindoline).

EXAMPLE 16

4'-Deoxyvinblastine

Under an argon atmosphere 0.180 g (0.170 mmol) of the 7S isomer of 5,7 PARF-5,2' PARF methyl 3-benzyl-1,2,3,4,5,6,7,8-octahydro-5-[2-(p.toluenesulfonyloxymethyl)butyl]-azonino(6,7-b)indole-7-(15-vindolinyl)-7-carboxylate in 25 mL of dry toluene was heated at reflux for 24 h with rapid stirring. At that point the starting amino tosylate had reacted completely. The cooled reaction mixture was concentrated under vacuum and the residual solid washed with three 50 mL portions of dry ether. The resulting quaternary salts, i.e. the 1'-equatorial and axial piperidine ring conformational isomer of 6'-benzyl-4'-deoxy-vinblastinonium tosylate (2'S,18'S) (0.172 g, 96%), which were free of starting amine by TLC, (ethyl acetate:ethanol, 1:1), were dissolved in 6 mL of methanol. Addition of 0.015 g of 10% Pd/charcoal and stirring under a hydrogen atmosphere at −20° C. for 40 min resulted in an uptake of 4 mL of hydrogen. The reaction mixture was filtered through a 1×3 cm plug of Celite 545, with subsequent washing of the Celite with 30 mL of methanol. Concentration at 20° C. under vacuum and solution of the residue in 50 mL of dichloromethane, washing of the solution with 2×30 mL of 3% ammonium hydroxide and satd. brine, drying (MgSO$_4$) filtration and concentration under vacuum gave 0.120 g of a mixture of 4'deoxyvinblastine and its bridged piperidine conformational isomer. This mixture was heated in 20 mL of toluene, under argon, for 4 h. Concentration under vacuum and centrifugal chromatography on a 2 mm silica gel plate, eluting with 3:1 ethyl acetate:ethanol at a flow rate of 2 mL/min, gave 6 mL of solvent followed by 34 mL of solution containing 0.052 g (41% yield) of the 1'-axial conformational isomer of 4'-deoxyvinblastine. UV (ethanol)λmax 225, 252, 288, 298 nm.

The compound 4'-deoxyvinblastine (191 mg) was converted to its methane sulfonate salt by first dissolving this compound in 10 mL of ether. To this solution was added 31 μl of methane sulfonic acid. The resulting precipitate was filtered and washed with 5 mL of ether providing 212 mg of the methane sulfonate salt of 4'-deoxyvinblastine.

EXAMPLE 17

Methyl 3-benzyl-1,2,3,3a,4,5-hexahydro-4(3-hydroxypropyl)-7H-pyrrolo(2,3-d) carbazole-6-carboxylate A mixture of methyl 3-benzyl-1,2,3,4,5,6-hexahydroazepino (4,5-b) indole-5-carboxylate (1.336 g, 4.0 mmol), 2-hydroxytetrahydropyran (0.980 g, 8.2 mmol), toluene (30 mL) and ether saturated with HCl gas (10 drops) was heated under a nitrogen atmosphere at 110° C. for 5 h. The reaction mixture was cooled, diluted with 15 mL of methanol and acidified with conc. hydrochloric acid. The reaction mixture was stirred for 12 h at 20° C., poured into 50 mL of water and made strongly basic with ammonium hydroxide. The toluene layer was separated and the aqueous portion extracted three times with 25 mL of dichloromethane. The combined organic solutions were washed three times with 25 mL of saturated brine, dried over sodium sulfate and concentrated at 50° C. under vacuum to provide 1.67 g (100%) of methyl 3-benzyl-1,2,3,3a,4,5-hexahydro-4-(3-hydroxypropyl)-7H-pyrrolo(2,3-d)carbazole-6-carboxylate, identical in spectroscopic properties and TLC R$_f$ value to the product obtained in Example 1.

EXAMPLE 18

4'-Deoxyvincristine

A solution of 4'-deoxyvinblastine methane sulfonate (21 mg, 0.023 mmol) in dichloromethane (2.5 mL) and acetic acid (320 μL, 5.6 mmol) was cooled to −78° C. and, with rapid stirring, a solution of potassium permanganate (8.2 mg, 0.052 mmol) and 1,4,7,10,13,16-hexaoxacyclooctadecane (17 mg, 64 mmol) in dichloromethane (1 mL) was added dropwise over 1 min. After 30 min at −78° C. the reaction mixture was poured into 50 mL of 4.5% sodium bisulfate solution at 0° C. and extracted with three 20 mL portions of cold dichloromethane. The combined organic extracts were washed with 50 mL of 8% sodium bicarbonate at 0° C., dried over magnesium sulfate and concentrated. Purification of the residue by high pressure liquid chromatography on a 50×2.5 cm 10μ SiO$_2$ column with 2:1 ethyl acetate:ethanol at 12 mL/min gave 8.0 mg (50% yield) of with TLC R$_f$0.34 (SiO$_2$, 2:1 ethyl acetate:ethanol), and mass spectroscopic m/z. M+ =808.

EXAMPLE 19

α-Methyl-δ-Valerolactone

A solution of 10.0 mL (10.79 g, 0.108 mmol) of δ valerolactone in 10 mL of dry tetrahydrofuran was added dropwise over 30 min to lithium diisopropylamide [prepared from 74.1 mL of 1.6 M(0.118 mmol) n-butyl lithium in hexane and 16.6 mL (0.118 mmol) of diisopropylamide] at −78° C. To the resulting salt suspension 6.72 mL (15.3 g, 0.108 mmol) of idomethane in 18.8 mL (19.3 g, 0.108 mmol) of hexamethylphosphoric triamide was added dropwise at −78° C. over 40 min, followed by stirring at −40° C. for 3 h. The mixture was then poured into 300 mL of saturated ammonium chloride and extracted with 3×100 mL of dichloromethane. The extracts were washed with 3×400 mL of water and 1×300 mL of saturated brine, dried (MgSO$_4$) and concentrated. The residual oil was chromatographed on 800 g of silica gel, ethyl acetate:pentane (3:2) to yield 10.1–10.7 g (82–87%) of the title compound NMR δ1.26 (d,d, 3H).

EXAMPLE 20

4-Carbomethoxy Valeraldehyde

To a stirred solution of 7.80 g (0.069 mol) of α-methyl-δ-valerolactone in 5 mL of dry methanol was added 6 mL of conc. sulfuric acid. After 20 min the mixture was neutralized with 200 mL of cold satd. sodium bicarbonate solution and extracted with 4×20 mL of cold dichloromethane. The cold extracts were dried (MgSO$_4$) and the solution immediately added to a stirring suspension of 53.99 g (2.7 equivalent) of pulverized pyridinium chlorochromate and 1.85 g (0.0226 mol) of sodium acetate in 80 mL of dry dichloromethane. After 30 min 3 g of silica gel was added and the slurry poured onto a 150 g silica gel column. Elution with ether, concentration of the eluate, solution of the residue in 20 mL of dichloromethane and washing of the solution with 3×30 mL of 1M HCl and 3×30 mL of satd. aqueous sodium bicarbonate, concentration and distillation gave 1.6–4.0 g (16–40%) of the title product, bp 90°–115° C. (0.6 mm); NMR δ6 9.75 (t, 1H).

EXAMPLE 21

Methyl 1,2,4,6-tetrahydro-11α and
β-11-[3-(carbomethoxy)butyl]-3,10b-
methanoazepino(4,5-b) indole-5-carboxylates A solution of 1.40 g (5.75 mmol) of methyl 1,2,3,4,5,6-hexahydroazepino (4,5-b) indole-5-carboxylate and 1.25 g (8.62 mmol) of 4-carbomethoxy valeraldehyde in 30 mL of dry methanol was stirred at 20° C. for 20 h. Concentration under vacuum and chromatography of the residue on 100 g of silica gel, eluting with ethyl acetate/pentane, 3:2, ethyl acetate, and ethyl acetate/ethanol, 4:1 provided 1.73–1.98 g (84–96%) of the two 11β epimeric products, with some separation of the 11α and 11β epimers. TLC (SiO₂) for 11α epimer $R_f$ 0.11 (ethyl acetate) and 11β epimer $R_f$ 0.39 (ethyl acetate); both CAS detection:blue-yellow center.

EXAMPLE 22

4,2' PREF and PARF Methyl
3-Benzyl-1,2,3,3a,4,5-hexahydro-4-[2-(carbomethoxy) propyl]-7H-pyrrolo (2,3-d) carbazole-6-carboxylate To 2.25 g (6.32 mmmol) of methyl 1,2,4,6-tetrahydro-11α and 11β[3 (carbomethoxy) butyl]-3,10b-methanoazipino (4, 5-b) indole-5-carboxylate in 50 mL of dry tetrahydrofuran was added 0.98 mL (8.21 mmol) of benzyl bromide and the mixture was then heated at reflux for two days. After concentration under vacuum, the residue was washed with ether and then taken up in 50 mL of dry methanol. After addition of 3.64 mL (26.2 mmol) of triethylamine, the solution was heated at reflux for 10 h. Concentration under vacuum and chromatography on 100 g of silica gel, eluting with ethyl acetate/pentane, 1:1, provided 2.55–2.70 g (85–90%) of the two 2'-epimeric products; TLC (SiO₂) $R_f$ 0.48 (ethyl acetate/pentane, 2:3), CAS blue, yellow center.

EXAMPLE 23

4,2' PREF and PARF Methyl
3-Benzyl-1,2,3,3a,4,5-hexahydro-4-[2-(hydroxymethyl) propyl]-7H-pyrrolo (2,3-d) carbazole-6-carboxylates At 0° C., 5.63 mL (5.63 mmol) of a 1M solution of lithium aluminum hydride in tetrahydrofuran was added dropwise over 10 min to 2.68 g (5.63 mmol) of 4,2' PREF and PARF methyl 3-benzyl- 1,2,3,3a,4,5-hexahydro-4-[2(carbomethoxy) propyl]-7H-pyrrolo (2,3,-d) carbazole-6-carboxylates in 50 mL of dry tetrahydrofuran. After 5 minutes the reaction mixture was poured into 10 mL of conc. ammonium hydroxide. Dilution with water, extraction with dichloromethane and concentration of the dried (MgSO₄) extracts gave 1.62 g (60%) of the two 2'-epimeric products. TLC (SiO₂) for the 4, 2' PARF alcohol $R_f$ 0.47 (ether/triethylamine, 9:1) and for the 4,2' PREF alcohol $R_f$ 0.33 (ether/triethylamine , 9:1), CAS blue. Using this solvent system, the two compounds were separated by low pressure chromatography to provide 0.78 g of the less polar titled 4, 2' PREF alcohol and 0.60 g of the more polar titled 4, 2' PARF alcohol.

EXAMPLE 24

4, 2' PREF and 4,2' PARF Methyl
3-Benzyl-1,2,3,3a,4,5-hexahydro-4-[2-(p-toluenesulfonyloxymethyl) propyl]-7H-pyrrolo]
(2,3-d)-carbazole-6-carboxylates To 0.78 (1.80 mmol) of 4,2'-PREF methyl 3-Benzyl-1,2,3,3a,4,5-hexahydro-4-[2-(hydroxymethyl)propyl]-7H-pyrrolo] (2,3-d)-carbazole-6-carboxylate in 20 mL of dichloromethane was added 0.30 g (0.43 mL) of triethylamine and 0.90 g (2.75 mmol) of P-toluenesulfonic anhydride. After 2.5 h the mixture was poured into 10% ammonium hydroxide in satd. brine and extracted with 3×50 mL of dichloromethane. The dried (Mg SO₄) and concentrated organic extracts were chromatographed on 70 g of silica gel, eluting with 1:2 ethyl acetate/pentane, to produce 0.77 g (73%) of the titled PREF tosylate; TLC (SiO₂) $R_f$ 0.30 (ethyl acetate/pentane, 2:3).

By the procedure of the above paragraph of this example 0.60 g (1.39 mmol) of the 4, 2'-PARF alcohol, was treated with 0.70 g (2.14 mmol) of p-toluenesulfonic anhydride and 0.25 g (0.33 mL) of triethylamine to give 0.56 g (69%) of the titled PARF tosylate product. TLC (SiO₂) $R_f$ 0.50 (ethyl acetate/pentane, 1:1).

EXAMPLE 25

4'-Deethyl-4'-deoxy-4'-S-methyl Vinblastine and its 2'R,4'R, 18'R-Diastereomer

At 0° C., 0.112 g (0.155 mL) of triethylamine was added to 0.434 g (0.737 mmol) of 4, 2'-PREF methyl 3-benzyl-1,2,3,3a,4,5-hexahydro-4-[2-(p-toluenesulfonyloxymethyl) propyl]-7H-pyrrolo (2, 3-d)-carbazole-6-carboxylate in 25 mL of dichloromethane, followed by 0.121 g (1.11 mmol) of t-butylhypochlorite. After 10 minutes the mixture was poured into water and extracted with dichloromethane. The dried (Mg SO₄) extract was concentrated under vacuum and the residue dissolved in 6 mL of dry acetone. At 0° C., 0.248 g (0.547 mmol) of vindoline was added, followed, after 10 min, by 0.17 g (1.05 mmol) of tetrafluoroboric acid diethyl ether complex. In the dark, 0.204 g (1.05 mmol) of solid silver tetrafluoroborate was added at 0° C., in two portions, over 15 minutes. After 20 minutes the mixture was partitioned between 10% ammonium hydroxide in brine and dichloromethane, and the extracts were dried and concentrated. The resultant crude 6S and 6R 4, 6-PARF-4, 2'-PREF methyl 3-benzyl-1,2,3,3a,4,5-hexahydro4-[2-(p-toluenesulfonyloxymethyl)propyl]-6-(15-vindolinyl)-pyrrolo(2,3-d)-carbazole-6-carboxylates were dissolved in 15 mL of acetic acid and at 20° C., 0.399 g (7.40 mmol) of potassium borohydride was added to the solution. The mixture was poured into an excess of conc. ammonium hydroxide and crushed ice and extracted with dichloromethane. The dried (MgSO₄) extracts were concentrated under vacuum and the residue was subjected to centrifugal chromatography on a 4 mm silica gel plate. Ether/acetone/triethylamine, 100:20:2, separated 0.362 g of the more polar titled 7R indole-indoline tosylate from unreacted vindoline and the less polar 7S product. Ethyl acetate/ethanol/triethylamine 95:5:1 parts by volume separated 0.304 g of the less polar 7S product from vindoline.

A mixture of 0.147 g (0.142 mmol) of the 7S product as in the title, and 20 mL of dry toluene was heated at reflux for seven days. The solvent was evaporated under vacuum and the residue triturated with ether to give 0.141 g (96%) of quaternary salts. This material was dissolved in 10 mL of methanol, 10 mg of 10% palladium on carbon was added, and the mixture was stirred under an atmosphere of hydrogen at 0°–20° C. for 3 h. The mixture was filtered through Celite, the filtrate was concentrated under vacuum and the residue dissolved in dichloromethane. The organic solution was washed with 10% ammonium hydroxide in satd. brine, concentrated and the residue centrifugally chromatographed on a 1 mm SiO$_2$ plate, eluting with 5% triethylamine in methanol to give 0.113 g (80% material. This was heated in toluene, at reflux for 12 h to provide 0.113 g (80%) of the titled product; TLC (SiO$_2$) R$_f$ 0.22 (5% triethylamine in methanol).

Heating of 0.096 g of the 7R indol-indoline tosylate, obtained in this reaction sequence, in 20 mL of toluene at reflux for 5 days gave 0.090 g (94%) of quaternary salts which, on hydrogenolysis in 15 mL of methanol with 20 mg of 10% Pd/C for 3 h gave 0.072 g (80%) of a mixture of the two piperdine conformational isomers of the 2'R, 4'R, 18'R titled product. The conformational isomer with the 4'-axial substitution [33 mg, TLC (SiO$_2$) R$_f$ 0.22 (5% triethylamine in methanol)] was separated from the more polar conformational isomer with 4'-equatorial conformation (36 mg) by centrifugal chromatography on a SiO$_2$ plate, eluting with 5% triethylamine in methanol. The latter product was converted to the former by heating in toluene at reflux. The 4'-axial substituted product of the title showed NMR (CDCl$_3$) δ0.65 (d, 3H) 0.32 (t, 3H).

EXAMPLE 26

4'-Deethyl-4'-deoxy-4'-R-methylvinblastine and its 2'-R, 4'-S, 18'-R diastereoisomer

Using the procedure of Example 25, 0.522 g (0.887 mmol) of 4,2'-PARF methyl 3-benzyl-1,2,3,3a,4,5-hexahydro-4-[2-p-toluenesulfonyloxymethyl) propyl]-7H-pyrrolo (2,3-d)-carbazole-6-carboxylate on reaction with 0.141 g (1.29 mmol) of t-butyl hypochlorite and 0.136 g ((0.187 mL) of triethylamine in 25 mL of dichloromethane, followed by a reaction with 0.297 g (0.654 mmol) of vindoline, 0.204 g (1.29 g mmol) of tetrafluoroboric acid diethyl ether complex and 0.245 g (1.26 mmol) of silver tetrafluoroborate in 6 mL of acetone, followed by reduction with 0.453 g (8.42 mmol) of potassium borohydride in 15 mL of acetic acid gave 0.276 g (41%) of the more polar 7R indole-indoline product, eluted on centrifugal chromatography with ether/acetone/triethylamine, 100:20:2, and 0.264 g(39%) of the less polar 7S indole-indoline product, eluted with ethyl acetate/ethanol/triethylamine 95:5:1.

Heating of 0.048 g of the 7S, 4,2'-PARF tosylate in 20 mL of toluene for 20 h and hydrogenolysis of the resulting 0.41 g (85%) salts with 10 mg of 10% Pd/C in 10 mL of methanol provided a product which was purified by centrifugal chromatography on a 1 mm SiO$_2$ plate, eluting with 5% triethylamine in methanol, to produce the 0.016 g of the 18'-S title compound with the 1'-axial conformation and 0.002 g of the 18'-S title compound with the 1'-equatorial conformation. The latter was converted to the former product on heating in toluene at reflux. The 1'-axial product showed NMR (CDCl$_3$) δ0.75 (t,3H), 0.65 (d, 3H).

Heating of 0.035 g of the 7R,4,2'-PARF tosylate in 20 mL of toluene at reflux for 17 h and hydrogenolysis of the resulting salts, 0.030 g (86%), with 10 mg of 10% Pd/C in 10 mL of methanol provided a mixture of conformational isomers for the 18'R title product. Centrifugal chromatography of this mixture on a 1 mm SiO$_2$ plate and elution with 5% triethylamine in methanol gave 0.012 g of the 1' equatorial 18'R title compound. The latter was converted to the former by heating in toluene at reflux. The 1'-axial product showed NMR (CDCl$_3$) δ0.65 (d,3H), 0.33 (t, 3H).

EXAMPLE 27

N-[1-(E)-Penten-1-yl]pyrrolidine To 200 mL (170.4 g, 2.40 mol) of rapidly stirred pyrrolidine at 3° C., under argon, was added 100 g (0.72 mmol) of potassium carbonate followed by 127 mL (102.9 g, 1.19 mol) of valeraldehyde dropwise over 75 min. After stirring at 3°-5° C. for 6 hr, the suspension was stored at ca. 0° C. for 64 hr, filtered and the collected solids were washed with 2×50 mL of anhydrous ether. The combined filtrates were concentrated in vacuo and the residue was distilled to give 142.32 g (85.7%) of N-[1-(E)-penten-1-yl]pyrrolidine, bp 54°-56° C. (0.6-0.7 mm Hg).

EXAMPLE 28

4-Formylheptanenitrile

A solution of 142.23 g (1.02 mol) of N-[1-(E)-penten-1-yl]pyrrolidine and 100 mL (80.6 g, 1.52 mol) of acrylonitrile in 570 mL of 1,4-dioxane was heated at gentle reflux, under argon, for 16 hr. 50 mL of water was then added and the mixture was stirred at reflux for a further 8 hr. After concentration in vacuo, 200 g of ice, 400 mL of 3N hydrogen chloride solution, and 600 mL of methylene chloride were added, and the mixture was stirred for 15 min. The aqueous layer was separated and extracted with 3×300 mL of methylene chloride, and the combined organic layers were washed with 2×150 mL of saturated brine, dried (MgSO$_4$), filtered and concentrated. The residue (140.2 g) was distilled to give 46.96 g (33.0%) of 4-formylheptanenitrile bp 103°-104° C. (1.33 mm Hg).

EXAMPLE 29

4-(Hydroxymethyl)heptanenitrile

To a solution of 46.94 g (0.338 mol) of 4-formylheptanenitrile in 250 mL of methanol at 3° C., under argon, was added 4.55 g (0.120 mol) of sodium borohydride portionwise over 1 hr. After stirring at 5° C. for 1 hr, the reaction mixture was poured into a mixture of 100 g of ice and 200 mL of 2N hydrogen chloride solution and extracted with 500 mL of ether followed by 4×250 mL of ether. The combined extracts were washed with 2×150 mL of saturated brine, dried (Na$_2$SO$_4$), filtered and concentrated. The residue was dried (40° C./1.0 mm Hg) to give 45.50 g (95.6%) of crude 4-(hydroxymethyl)heptanenitrile; TLC ((SiO$_2$, 1:1 ethyl acetate:hexane) R$_f$ 0.28 (PMA); IR (chloroform): $\mu_{max}$ 3625 (OH), 3490 (OH), 2245 (C≡N) cm$^{-1}$.

EXAMPLE 30

4-(t-Butyldimethylsiloxymethyl)heptanenitrile

To a mixture of 45.50 g (0.323 mol) of crude 4-(hydroxymethyl)heptanenitrile and 53.5 g of t-butyldimethylsilyl chloride in 450 mL of methylene chloride at 3°-4° C., under argon, was added a solution of 67.5 mL (50.1 g, 0.388 mol) of diisopropylethylamine in 67.5 mL of methylenechloride dropwise over 10 min. 3.94 g (32,2 mmol) of 4-dimethylaminopyridine was then added and after stirring at room temperature for 66 hr, the dark reaction mixture was washed with 150 mL of 2N hydrogen chloride solution, 150 mL of water and 150 mL of saturated brine, dried (MgSO$_4$), filtered, and concentrated. The residue was redissolved in methylene chloride, 180 g of silica gel was added and the solvent was removed under vacuum. The residual powder was placed on top of a 2⅜"×9" column of 270 g of silica gel and eluted, sequentially, with 1 L of hexane, 1 L of 1:19 ethyl acetate:hexane and 1 L of 1:9 ethyl acetate:hexane; 500-mL fractions were collected. Fractions 3-7 were combined and concentrated in vacuo, and the residue was distilled to give 68.22 g (82.9%) of 4-(t-butyldimethylsiloxymethyl)heptanenitrile, bp 114°–117° C. (0.9–1.0 mm Hg).

EXAMPLE 31

4-(t-Butyldimethylsiloxymethyl)heptanal

To a solution of 12.15 g (47.6 mmol) of 4-(t-butyldimethylsiloxymethyl)heptanenitrile in 120 mL of toluene at −70° C., under argon, was added 35.3 mL (53.0 mmol) of a 1.5 M solution of diisobutylaluminum hydride in toluene. After stirring at −70° C. for 3.25 hr, 36.5 mL of methanol was added and the mixture was poured into a mixture of ca. 200 mL of ether, ca. 100 g of ice and 214 mL of 3N hydrogen chloride solution. The aquenous layer was separated and extracted with 3×200 mL of ether. The combined organic layers were washed with 120 mL of saturated sodium bicarbonate solution and 120 mL of saturated brine (a gelatinous precipitate, which resulted on washing with saturated brine, was removed by filtration through celite prior to separation of the aqueous layer), dried ($Na_2SO_4$), filtered and concentrated. The residue was purified by column chromatography on silica gel to give 10.01 g (81.4%) of crude 4-(t-butyldimethylsiloxymethyl)heptanal; TLC ($SiO_2$, 1:9 ethyl acetate:hexane) Rf 0.55 (PMA); IR (chloroform): $\mu_{max}$ 1719 (adehyde C=O) $cm^{-1}$.

EXAMPLE 32

Racemic Methyl 1,2,4,6-Tetrahydro-11α,β[3-(t-butyldimethylsiloxymethyl)hexyl]-3.10b-methanoazepino (4,5-b)indole-5-carboxylate To a solution of 9.99 g (38.7 mmol) of 4-(t-butyldimethylsiloxymethyl)heptanal in 40 mL of methanol, under argon, was added 8,59 g (35.2 mmol) of methyl 1,2,3,4,5,6-hexahydroazepino(4,5-b)-indole-5-carboxylate. After stirring at room temperature for 19 hrs., the solvent was removed in vacuo. The residue was Purified by column chromatography on silica gel to give 17.45 g (quantitative) of crude racemic methyl 1,2,4,6-tetrahydro-11-α,β[3-(t-butyldimethylsiloxymethyl)hexyl]-3,10b-methanoazepino(4,5-b)indole-5-carboxylate; TLC ($SiO_2$, 37:3 chloroform:methanol) Rf 0.39 (PMA); IR (chloroform): $\mu_{max}$ 3445 (NH), 3405 (NH), 1680 (ester C=O) $cm^{-1}$; MS: m/e 484 (M+).

EXAMPLE 33 4,2′-PREF and 4,2′-PARF Methyl 3-Benzyl-1,2,3,3a,4,5-hexahydro-4[2-(t-butyldimethylsiloxymethyl)pentyl]-7H-pyrrolo (2,3-d)carbazole-6-carboxylate To a solution of 17,45 g of crude methyl 1,2,4,6-tetrahydro-11-[2-(t-butyldimethylsiloxymethyl)hexyl]-3,10b-methanoazepino (4,5-b)indole-5-carboxylate in 340 mL of dry tetrahydrofuran was added 5 mL (7.12 g, 41.6 mmol) of benzyl bromide. The reaction mixture was stirred at room temperature, under argon, for 19 hrs., then concentrated and the residual white solid, the quaternary salt 3-benzyl-1,2,4,6-tetrahydro-11-[2-(t-butyldimethylsiloxymethyl)hexyl]-3,10b-methanoazepino (4,5-b)indolium bromide, was dissolved in 240 mL of methanol. 11 mL (8.00 g, 61.9 mmol) of diisopropylethylamine was added and the reaction mixture was heated to reflux, under argon, for 3 hr. The solvent was removed in vacuo and the residue was purified by column chromatography on silica gel to give 16.48 g (81.6% from methyl 1,2,3,4,5,6-hexahydroazepino (4,5-b)indole-5-carboxylate) of a diastereomeric mixture of 4-2′-PREF and 4,2′-PARF methyl 3-benzyl-1,2,3,3a,4,5-hexahydro-4[2-(t-butyldimethylsiloxymethyl)pentyl]-7H-pyrrolo (2,3-d)carbazole-6-carboxylate; TLC ($SiO_2$, 1:9 ethyl acetate:hexane) Rf 0.28 (PMA); IR (chloroform): $\mu_{max}$ 3390 (NH) 1672 (ester C=O) $cm^{-1}$. MS: m/e 574 (M+).

EXAMPLE 34

4,2′-PREF and 4,2′-PARF Methyl 3-Benzyl-1,2,3,3a,4,5-hexahydro-42-(hydroxymethyl)-pentyll-7H-pyrrolo (2,3-d)carbazole-6-carboxylate To a solution of 16.46 g (28.7 mmol) of a mixture of 4,2′-PREF and 4,2′-PARF methyl 3-benzyl-1,2,3,3a,4,5-hexahydro-4[2-(t-butyldimethylsiloxymethyl)pentyl]-7H-pyrrolo (2,3-d)carbazole-6-carboxylate in 170 mL of acetonitrile was added 8.2 g (87.1 mmol) of potassium fluoride dihydrate, followed by 21.5 g (91.6 mmol) of benzyltriethylammonium chloride. The reaction mixture was heated to reflux, under argon, for 48 hr, then concentrated. The residue was purified by column chromatography on silica gel to give 10.85 g (82.3%) of a diastereomeric mixture of 4,2′-PREF and 4,2′-PARF methyl 3-benzyl-1,2,3,3a,4,5-hexahydro-4[2-(hydroxymethyl) pentyl]-7H-pyrrolo-(2,3-d)carbazole-6-carboxylate; TLC ($SiO_2$, 1:1 ethyl acetate:hexane) Rf 0.50 (PMA); IR (chloroform $\mu_{max}$ 3620 (OH), 3380 (NH), 1672 (ester C=O) $cm^{-1}$.

EXAMPLE 35

4,2′-PREF and 4,2′-PARF Methyl 3-benzyl-1,2,3,3a,4,5-hexahydro-4[2-(p-toluenesulfonyloxymethyl)pentyl]-7H-pyrrolo (2,3-d)carbazole-6-carboxylate To a solution of 10,85 g (23.6 mmol) of a mixture of 4,2′-PREF and 4,2′-PARF methyl 3-benzyl-1,2,3,3a,4,5-hexahydro-4[2-(hydroxymethyl)pentyl]-7H-pyrrolo(2,3-d)carbazole-6-carboxylate in 45 mL of dry pyridine was added 7.4 g (38.8 mmole) of p-toluenesulfonyl chloride, followed by 290 mg (2.35 mmol) of 4-dimethylaminopyridine. After stirring at room temperature, under argon, for 26 hr, the reaction mixture was diluted with 350 mL of methylene chloride, washed with 100 mL of 10% ammonium hydroxide solution and 2×100 mL of saturated brine, dried ($Na_2SO_4$), filtered and concentrated. The residue was purified by column chromatography on silica gel to give 11.11 g (76.7%) of a diastereomeric mixture of 4,2′-PREF and 4,2′-PARF methyl 3-benzyl-1,2,3,3a,4,5-hexahydro-4[2-(p-toluenesulfonyloxymethyl)pentyl]-7H-pyrrolo(2,3-d)carbazole-6-carboxylate; TLC ($SiO_2$, 1:4 ethyl acetate: hexane) Rf 0.25 (PMA); IR (chloroform) $\mu_{max}$ 3385 (NH), 1672 (ester C=O) $cm^{-1}$.

This mixture of tosylates was separated by preparative high pressure liquid chromatography (PrepPak-500/silica) to give 3.92 g (35.3% recovery) of predominantly the 4,2′-PARF isomer and 4.45 g (40.1% recovery of predominantly the 4,2′-PREF isomer.

EXAMPLE 36

6S and 6R Isomers of 4,6-PARF, 4,2'-PARF Methyl 3-Benzyl-1,2,3,3a,4,5-hexahydro-4-[2-(p-toluenesulfonyloxymethyl)pentyl]-6-(15-vindolinyl)pyrrolo(2.3-d)carbazole-6-carboxylate To a solution of 3.87 g (6.30 mmol) of predominantly 4,2'-PARF methyl 3-benzyl-1,2,3,3a,4,5-hexahydro-4[2-(p-toluenesulfonyloxymethyl)pentyl]-7H-pyrrolo(2,3-d)carbazole-6-carboxylate and 0.91 mL (0.654 g, 6.46 mmol) of triethylamine in 80 mL of methylene chloride at 0° C., under argon, was added 0.97 ml (8.20 mmol) of t-butylhypochlorite. After stirring at 0° C. for 1 hr, the reaction mixture was washed with 2×80 mL of water and 80 mL of saturated brine, dried ($Na_2SO_4$), filtered, and concentrated to give 4.00 g (97.9%) of methyl 3-benzyl-6-chloro-1,2,3,3a,4,5-hexahydro-4-[2-(p-toluenesulfonyloxymethyl)pentyl]pyrrolo-6-carboxylate.

To a solution of 1.94 g (4.25 mmol) of vindoline in 35 mL of methylene chloride was added methylene chloride saturated with hydrogen chloride until litmus paper indicated that the pH of the solution was less than pH 2. The solvent was removed in vacuo, 30 mL of acetone was added and the solution was reconcentrated. The residual white solid, the hydrogen chloride salt of vindoline, was redissolved in 70 mL of acetone and added to 4.00 g (6.17 mmol) of the chloroindolenine from above. 3.7 g (19.0 mmol) of silver tetrafluoroborate was then added and reaction mixture was stirred at room temperature, under argon, for 80 min. After the addition of 45 mL of conc. ammonium hydroxide solution, 45 mL of water and 45 mL of saturated brine, the mixture was extracted with 3×90 mL of methylene chloride and the combined extracts were washed with 90 mL of saturated brine, dried ($Na_2SO_4$), filtered and concentrated under vacuum. The residue was purified by column chromatography on silica gel to give 3.04 g (66.9% from vindoline) of the 6S and 6R isomers of 4,6-PARF, 4,2'-PARF methyl 3-benzyl-1,2,3,3a,4,5-hexahydro-4-[2-(p-toluenesulfonyloxymethyl)pentyl]-6-(15-vindolinyl)pyrrolo(2,3-d)-carbazole-6-carboxylate;TLC ($SiO_2$, 1:1 acetone:hexane) Rf 0.44 (PMA).

EXAMPLE 37

7S and 7R Isomers of 5.7-PARF. 5.2'-PARF Methyl 3-Benzyl-1,2,3,4,5,6,7,8-octahydro-5-[2-(p-toluenesulfonyloxymethyl)pentyl]azonino(6.7-b)indole-7-(15-vindolinyl)-7-carboxylate To a solution of 2.99 g (2.80 mmol) of the 6S and 6R Isomers of 4,6-PARF, 4,2'-PARF methyl 3-benzyl-1,2,3,3a, 4,5-hexahydro-4-[2-(p-toluenesulfonyloxymethyl)pentyl]-6-(15 -vindolinyl)pyrrolo(2,3-d)carbazole-6-carboxylate in 70 mL of glacial acetic acid was added portionwise, under argon, 1.33 g (35.2 mmol) of sodium borohydride. After stirring at room temperature for 30 min, a further 0.332 g (8.78 mmol) of sodium borohydride was added and stirring was continued for 15 min. The reaction mixture was then poured on to ca. 100 g of ice, basified to pH 9-10 with conc. ammonium hydroxide solution, and extracted with 2×100 mL followed by 40 mL of methylene chloride. The combined extracts were washed with 3×100 mL of water and 100 mL of saturated brine, dried ($Na_2SO_4$), filtered, and concentrated to give 3.08 g of a mixture of the 7S and 7R isomers of 5,7-PARF, 5,2'-PARF methyl 3-benzyl-1,2,3,4,5,6,7,8-octahydro-5-[2-(p-toluenesulfonyloxymethyl)pentyl]azonino(6,7-b)indole-7-(15-vindolinyl)-7-carboxylate. This material was purified by column chromatography on silica gel to give 1.32 g (44.0%) of the 7S isomer, 1.56 g (52%) of mixed fractions, and 153 mg (5.11%) of the 7R isomer. Rechromatography of the mixed fractions provided additional separated compounds, for a combined total of 1.67 g (55.7%) of the 7S isomer of 5,7-PARF, 5,2'-PARF methyl 3-benzyl-1,2,3,4,5,6,7,8-octahydro-5-[2-(p-toluenesulfonyloxymethyl)pentyl]azonino(6.7-b)indole-7-(15-vindolinyl)-7-carboxylate [TLC ($SiO_2$, ethyl acetate) Rf 0.70 (PMA)] plus 0.577 g (14.2%) of the corresponding 7R isomer [TLC ($SiO_2$, ethyl acetate) Rf 0.51 (PMA)].

EXAMPLE 38

4'-Deoxy-4'-deethyl-4'R-n-propylvinblastine

A solution of 1.63 g (15.2 mmol) of the 7S isomer of 5,7-PARF, 5,2'-PARF methyl 3-benzyl-1,2,3,4,5,6,7,8-octahydro-5-[2-(p-toluenesulfonyloxymethyl)pentyl]azonino(6,7-b)indole-7-(15-vindolinyl)-7-carboxylate in 225 mL of xylene was heated at 140° C., under argon, for 22 hr. After allowing to cool to room temperature, the solvent was removed in vacuo and the residual solid was washed with 3×450 mL of ether to give 1.138 g (69.8%) of the quaternary salt, 6'-benzyl-4'-deoxy-4'-deethyl-4'R-n-propyl-vinblastine tosylate (2'S, 18'S).

The quaternary salt was dissolved in 37.7 mL of methanol, 87 mg of 10% Pd-charcoal was added and the mixture was stirred under an atmosphere of hydrogen at room temperature for 5½ hr. The reaction mixture was filtered through a plug of celite, and the plug plus collected solids were washed with methanol. The combined filtrates were concentrated and the residue was redissolved in methanol and rehydrogenated as described above. The crude Product, after the second hydrogenation, was dissolved in 300 mL of methylene chloride and the resulting solution was washed with 2×180 mL of 3% ammonium hydroxide solution and 2×180 mL of saturated brine, dried ($MgSO_4$), filtered, and concentrated under vacuum. The residual oil was dissolved in 140 mL of toluene and the resulting solution was heated at reflux for 4 hr, then concentrated. The residue was purified by two column chromatographies on silica gel to give 460 mg (37.4%) of -4'-deoxy-4.-deethyl-4'R-n-propyl-vinblastine; TLC ($SiO_2$, 3:1 ethyl acetate:ethanol) Rf 0.38 (PMA); IR (chloroform): $\mu_{max}$ 3465 (NH), 1738 (ester C=O) $cm^{-1}$.

EXAMPLE 39

4'-Deoxy-4'-deethyl-4'R-n-propyl-vinblastine Methanesulfonate

To a solution of 200 mg (0.25 mmol) of 4'-deoxy-4'-deethyl-4'R-n-propylvinblastine in 10 mL of methylene chloride, under argon, was added 1.61 mL (0.50 mmol) of a solution of 1 mL of methanesulfonic acid in 50 mL of methylene chloride. The solvent was removed in vacuo, 25 mL of anhydrous ether and 3 mL of methanol were added to the residue and after standing overnight at ca. 0° C., the mixture was reconcentrated. 20 mL of anhydrous ether was added to the residue and the resulting precipitate was collected by filtration, washed with 2×10 mL of ether, and dried under vacuum (1.0 mm Hg) to give 207 mg of 4'-deoxy-4'-deethyl-4'R-n-propylvinblastine methanesulfonate, mp 206°-207° C.

EXAMPLE 40

4′-Deoxy-4′-deethyl-4′R-n-propyl-vincristine

A solution of 201.7 mg (0.223 mmol) of 4′-deoxy-4′-deethyl-4′R-n-propylvinblastine methanesulfonate and 3.1 mL (54.2 mmol) of acetic acid in 24 mL of methylene chloride was cooled to -72° C., under argon, and a solution of 80 mg (0.506 mmol) of potassium permanganate and 165 mg (0.624 mmol) of 1,4,7,10,13,16-hexaoxacyclooctadecane in 10 mL of methylene chloride was added dropwise over 15 min. After stirring at −71° C. for 45 min, the reaction mixture was poured into 500 mL of 4.5% sodium bisulfote solution at 0° C. and extracted with 3×190 mL of cold methylene chloride. The combined extracts were washed with 500 mL of cold 8% sodium bicarbonate solution, dried (MgSO$_4$) filtered and concentrated. The residue was purified by column chromatography on silica gel to give 68.9 mg of 4′-deoxy-4′-deethyl-4′R-n-propylvincristine, mp 201°–203° C., TLC (SiO$_2$, 1:1 acetone) Rf 0.33 (PMA); IR (KBr): $\mu_{max}$ 3450 (broad, NH and OH), 1740 (ester C=O), 1680 (amide C=O) cm$^{-1}$.

EXAMPLE 41

4′-Deoxy-4′-deethyl-4′R-n-propylvincristine Methanesulfonate

To a solution of 68.9 mg (0.084 mmol) of 4′-deoxy-4′-deethyl-4′R-n-propylvincristine in 5 mL of methylene chloride, under argon, was added 0.55 mL (0.170 mmol) of a solution of 1 mL of methanesulfonic acid in 50 mL of methylene chloride. The reaction mixture was concentrated and the residue was triturated with anhydrous ether. The solid was collected by filtration, washed well with ether, and dried under vacuum (1.0 mm) to give 52.7 mg of 4′-deoxy-4′-deethyl-4′R-n-propylvincristine methanesulfonate, mp 213°–215° C.; IR (KBr): $\mu_{max}$ 3430 (NH and OH), 1742 (ester C=O), 1678 (amide C=O), 1217 and 1042 (SO$_3$) cm$^{-1}$.

EXAMPLE 42

6S and 6R Isomers of 4.6-PARF. 4.2′-PREF Methyl 3-Benzyl-1,2,3,3a,4,5-hexahydro-4-[2-(p-toluenesulfonyloxymethyl) pentyl]-6-(15-vindolinyl)pyrrolo(2,3-d)carbazole-6carboxylate To a solution of 4.39 g (7.15 mmol) of predominantly 4,2′-PREF methyl 3-benzyl-1,2,3,3a,4,5-hexahydro-4-[2-(p-toluenesulfonyloxymethyl)pentyl]-7H-pyrrolo(2,3-d) carbazole-6-carboxylate and 1.03 mL (0.74 g, 7.32 mmol) of triethylamine in 80 mL of methylene chloride at 0° C., under argon, was added 1.1 mL (9.30 mmol) of t-butylhypochlorite. After stirring at 0° C. for 1 hr, the reaction mixture was washed with 2×80 mL of water and 80 mL of saturated brine, dried (Na$_2$SO$_4$), filtered, and concentrated to give 4.91 g (quantitative) of methyl 3-benzyl-6-chloro-1,2,3,3a,4,5-hexahydro-4-[2-(p-toluenesulfonyloxymethyl)pentyl]pyrrolo-6-carboxylate.

To a solution of 2.25 g (4.93 mmol) of vindoline in 35 mL of methylene chloride was added methylene chloride saturated with hydrogen chloride until litmus paper indicated that the pH of the solution was less than pH 2. The solvent was removed in vacuo, 30 mL of acetone was added and the solution was reconcentrated. The residual white solid, the hydrogen chloride salt of vindoline, was redissolved in 80 mL of acetone and added to 4.91 g of the chloroindolenine from above. 4.29 g (22.0 mmol) of silver tetrafluoroborate was then added and reaction mixture was stirred at room temperature, under argon, for 1 hr. After the addition of 50 mL of conc. ammonium hydroxide solution, 50 mL of water and 50 mL of saturated brine, the mixture was extracted with 3×100 mL of methylene chloride and the combined extracts were washed with 100 mL of saturated brine, dried (Na$_2$SO$_4$), filtered and concentrated under vacuum. The residue was purified by column chromatography on silica gel to give 4.24 g (80.5% from vindoline) of the 6S and 6R isomers of 4,6-PARF, 4,2′-PREF methyl 3-benzyl-1,2,3,3a,4,5-hexahydro-4-[2-(p-toluenesulfonyloxymethyl)pentyl]-6-(15-vindolinyl) pyrrolo(2,3-d)-carbazole-6-carboxylate; TLC (SiO$_2$, 1:1 acetone:hexane) Rf 0.44 (PMA).

EXAMPLE 43

7S and 7R Isomers of 5.7-PARF. 5.2′-PREF Methyl 3-Benzyl-1.2,3,4,5,6,7,8-octahydro-5-2-(p-toluenesulfonyloxymethyl) pentyl]azonino(6.7-b)indole-7-(15-vindolinyl)-7-carboxylate To a solution of 4.19 g (3.92 mmol) of the 6S and 6R Isomers of 4,6-PARF, 4,2′-PREF methyl 3-benzyl-1,2,3,3a,4,5-hexahydro-4-[2-(p-toluenesulfonyloxymethyl)pentyl]-6-(15 vindolinyl)pyrrolo(2,3-d)carbazole-6-carboxylate in 70 mL of glacial acetic acid was added portionwise, under argon, 1.87 g (49.4 mmol) of sodium borohydride. After stirring at room temperature for 45 min, a further 0.465 g (12.3 mmol) of sodium borohydride was added and stirring was continued for 50 min. The reaction mixture was then poured on to ca. 100 g of ice, basified to pH 9–10 with conc. ammonium hydroxide solution, and extracted with 2×100 mL followed by 50 mL of methylene chloride. The combined extracts were washed with 3×120 mL of water and 100 mL of saturated brine, dried (Na$_2$SO$_4$), filtered, and concentrated to give 4.15 g (98.9%) of a mixture of the 7S and 7R isomers of 5,7-PARF, 5,2.-PREF methyl 3-benzyl-1,2,3,4,5,6,7,8-octahydro-5-[2-(p-toluenesulfonyloxymethyl)pentyl]azonino(6,7-b)indole-7-(15-vindolinyl)-7carboxylate. This material was purified by column chromatography on silica gel to give 1.82 g of Predominantly the 7S isomer, 1.78 g of mixed fractions, and 0.49 g of predominatly the 7R isomer. Rechromatography then gave 1.76 g (41.9%) of the 7S isomer of 5,7-PARF, 5,2′-PREF methyl 3-benzyl-1,2,3,4,5,6,7,8-octahydro-5-[2-(p-toluenesulfonyloxymethyl)pentyl]azonino(6,7-b)indole-7-(15-vindolinyl)-7-carboxylate [TLC (SiO$_2$, ethyl acetate) Rf 0.72 (PMA)] plus 0.93 g (22%) of the corresponding 7R isomer [TLC (SiO$_2$, ethyl acetate) Rf 0.62 (PMA)].

EXAMPLE 44

4′-Deoxy-4′-deethyl-4′S-n-propyl-vinblastine

A solution of 1.65 g (15.4 mmol) of the 7S isomer of 5,7-PARF, 5,2′-PREF methyl 3-benzyl-1,2,3,4,5,6,7,8-octahydro-5-[2-(p-toluenesulfonyloxymethyl)pentyl-]azonino (6,7-b)indole-7-(15-vindolinyl)-7-carboxylate in 225 mL of xylene was heated at 140° C., under argon, for 22 hr. After allowing to cool to room temperature, the solvent was removed in vacuo and the residual solid was washed with 5×250 mL of ether to give 1.09 g (66.1%) of the quaternary salt, 6′-benzyl-4′-deoxy-4′-deethyl-4′S-n-propylvinblastine tosylate (2′S, 18′S).

The quaternary salt was dissolved in 36 mL of methanol, 84 mg of 10% Pd-charcoal was added and the mixture was stirred under an atmosphere of hydrogen at room temperature for 6½ hr. The reaction mixture was filtered through a plug of Celite, and the plug plus collected solids were washed with methanol. The combined filtrates were concentrated under vacuum and the residue was redissolved in methanol and rehydrogenated as described above. The crude product, after the second hydrogenation, was dissolved in 300 mL of methylene chloride and the resulting solution was washed with 2×180 mL of 3% ammonium hydroxide solution and 2×180 mL of saturated brine, dried (MgSO₄), filtered, and concentrated under vacuum. he residual oil was dissolved in 120 mL of toluene and the resulting solution was heated at reflux for 4½ hr and concentrated. The residue was purified by two column chromatographies on silica gel to give 334.5 mg (40.6%) of 4'-deoxy-4'-deethyl-4'S-n-propylvinblastine; TLC (SiO₂, 3:1 ethyl acetate:ethanol) Rf 0.11 (PMA); IR (chloroform): $\mu_{max}$ 3465 (NH), 1738 (ester C=O) cm$^{-1}$.

EXAMPLE 45
4'-Deoxy-4'-deethyl-4'S-n-propylvinblastine methanesulfonate

To a solution of 100 mg (0.124 mmol) of 4'-deoxy-4'-deethyl-4'S-n-propylvinblastine in 5 mL of methylene chloride, under argon, was added 0.81 mL (0.24 mmol) of a solution of 1 mL of methanesulfonic acid in 50 mL of methylene chloride. The solvent was removed in vacuo, 25 mL of anhydrous ether and 3 mL of methanol were added to the residue and after standing overnight at ca. 0° C., the precipitate was collected by filteration, washed with 5 mL of ether, and dried under vacuum (1.0 mm Hg) to give 35.9 mg of 4'-deoxy-4'-deethyl-4'S-n-propyl-vinblastine methanesulfonate, mp 237°–239° C. The combined filtrates from above were concentrated and the residue was triturated with ca. 10 mL of ether. The precipitate was collected by filtration, washed with 2×10 mL of ether, and dried in vacuo (1.0 mm Hg) to give a further 67.7 mg of 4'-deoxy-4'-deethyl-4'S-n-propylvinblastine methanesulfonate.

EXAMPLE 46
4'-Deoxy-4'-deethyl-4'S-n-propylvincristine

A solution of 139.6 mg of 4'-deoxy-4'-deethyl-4'S-n-propylvinblastine methanesulfonate and 2.2 mL (38.4 mmol) acetic acid in 19 mL of methylene chloride was cooled to −72° C., under argon, and a solution of 56 mg (0.354 mmol) of potassium permanganate and 115 mg (0.431 mmol) of 1,4,7,10,13,16-hexaoxacyclooctadecane in 8 mL of methylene chloride was added dropwise over 10 min. After stirring at −71° C. for 1 hr, the reaction mixture was poured into 335 mL of 4.5% sodium bisulfite solution at 0° C. and extracted with 6×135 mL of cold methylene chloride. The combined extracts were washed with 335 mL of cold 8% sodium bicarbonate solution, dried (MgSO₄) filtered and concentrated. The residue was purified by column chromatography on silica gel to give 71.0 mg of 4'-deoxy-4'-deethyl-4'S-n-propylvincristine, mp 233°–235° C.; TLC (SiO₂, 1:1 acetone:hexane) Rf 0.04 (PMA); IR (KBr): $\lambda_{max}$ 3465 (broad, NH and OH), 1738 (ester C=O), 1678 (amide C=O) cm$^{-1}$.

EXAMPLE 47
4'-Deoxy-4'-deethyl-4'S-n-propylvincristine methanesulfonate

To a solution of 71.0 mg (0.084 mmol) of 4'-deoxy-4'-deethyl-4'S-n-propylvincristine in 5 mL of methylene chloride, under argon, was added 0.57 mL (0.176 mmol) of a solution of 1 mL of methanesulfonic acid in 50 mL of methylene chloride. The reaction mixture was concentrated and the residue was triturated with anhydrous ether. The solid was collected by filtration, washed with ether, and dried under vacuum (1.0 mm) to give 58.2 mg of 4'-deoxy-4'-deethyl-4'S-n-propylvincristine methanesulfonate, mp 232°–233° C.; IR (KBr): $\mu_{max}$ 3440 (NH and OH), 1750 (ester C=O), 1680 (amide C=O), 1210 SO₃) cm$^{-1}$.

EXAMPLE 48
4,4-Dimethyl-5-oxovaleronitrile

To a solution of 64.8 g (0.898 mmol, 51.45 mL) of isobutyraldehyde in 300 mL of dry dioxane was added 300 mg of hydroquinone (0.0027 mmol) and 60.0 g (1.13 mmol; 1.26 eq; 48.4 mL) of acrylonitrile. To this stirred solution was added all at once a freshly prepared solution of 3 g of NaOH dissolved in 60 mL of water and the whole was heated at 65° C. during 150 min. After cooling to 20° C., removal of the solvents under aspirator vacuum gave a residue which was partitioned between water and CH₂Cl₂. After separation, the aqueous layer was extracted 3 times with CH₂Cl₂ and the combined organic layers dried over Na₂SO₄ and concentrated under vacuum (aspirator). The crude residue was distilled under vacuum 81° C./1mm Hg) to yield 54 g (49%) of 4,4-dimethyl-5-oxovaleronitrile.

EXAMPLE 49
4,4-Dimethyl-5-hydroxyvaleronitrile

To a solution of 47 g (0.376 mmol) of 4,4-dimethyl-5-oxovaleronitrile in 350 mL of methanol, cooled to 0° C. (ice bath), was added, with vigorous stirring and over 15–20 min., 7.9 g (0.209 mmol; 2.22 hydride equiv.) of NaBH₄. After the addition was completed, the solution was stirred an additional 30 min. at 0° C. before removing the solvent in vacuo (aspirator . To the residue was added CH₂Cl₂ followed by careful addition of H₂O, and finally 1.2N HCl until pH=1–2 was obtained. The layers were separated and the aqueous one extracted twice (CH₂Cl₂), saturated with NaCl and extracted again three times with CH₂Cl₂. After drying the combined organic layers over Na₂SO₄ and removing the solvent under vacuum (aspirator) 47.7 g (95%) of the title compound, sufficiently pure for the next step, was obtained as a faint yellow oil. TLC: (Silica) R$_f$=0.26 (ethyl acetate dichloromethane 1:9), detection with molybdophosphoric acid (yellow spot on blue-green).

EXAMPLE 50
4,4-Dimethyl-5-t-butyldimethylsilyloxyvaleronitrile

To a solution of 16.13 g (0.127 mmol) of 4,4-dimethyl-5-hydroxyvaleronitrile in 250 mL of dry CH₂Cl₂ was added, at 20° C., in 2 min., 24.2 mL (0.139 mmol; 1.09 eq) of diisopropylethylamine, followed after 5 min. by 25.0 g (0.165 mmol; 1.3 eq) of solid t-butyldimethylsilyl chloride, all at once. Then, 1.55 g (0.0127 mmol; 0.1 eq) of 4-dimethylaminopyridine was added and the whole was stirred at 20° C. during 18h. After removing the solvent under vacuum (aspirator) the brown residue was taken up in H₂O, followed by ethyl ether. The layers were separated and the aqueous one extracted three times with 200 mL of ether. The combined organic layers were back extracted with water (100 mL), HCl 1.2N (100 mL), 5% KHCO₃ (2×100 mL), dried over Na₂SO₄ and concentrated under vacuum to give a faint yellow oil. Distillation at 94°–97° C. (0.7 mm) gave 21 g (69%) of the title compound. TLC: (Silica), R$_f$0.59 (CH₂Cl₂), detection with molybdophosphoric acid blue on yellow.

EXAMPLE 51

4,4-Dimethyl-5-t-butyldimethylsilyloxyvaleraldehyde

To a cooled (-78° C.) solution of 4.5 g (18.6 mmol) of 4,4-dimethyl-5-t-butyldimethylsilyloxyvaleronitrile in 36 mL of dry CH₂Cl₂ was added dropwise, over 30 min., 20.4 mL (20.4 mmol; 1.1 eq) of a 1.0 M solution of diisobutyl-aluminum hydride in CH₂Cl₂. After stirring for 2 h at −78° C., the cooling bath was removed and the solution allowed to warm to 0° C. To the crude (0° C.) reaction mixture was added 50–60 mL of ethyl ether, followed by the cautious addition of 10% HCl, until the mixture became strongly acidic (pH=1–2). Separation of the layers and three extractions of the aqueous phase with 100 mL ether, drying over MgSO₄ and concentrating the combined organic layers gave 3.6 g (79%) of the title compound as a faint yellow oil, sufficiently pure to be used in the next step. TLC: (Silica) R$_f$0.28 (CH₂/Cl₂/pentane 3:7), detection with Purpald.

EXAMPLE 52

Methyl 3-Benzyl-1,2,3,3a,4,5-hexahydro-4[2.2-dimethyl-3-(t-butyldimethylsilyloxy)propyl]-7H-pyrrolo(2,3-d)carbazole-6-carboxylate To a solution of 3.5 g (14.3 mmol) of methyl 1,2,3,4,5,6-hexahydroazepino(4,5-b)indole-5-carboxylate in 175 mL of dry CH₂Cl₂ at 20° C. was added dropwise, over 2 min., 3.5 g (14.3 mmol, 1 eq) of 4,4-dimethyl-5-t-butyldimethylsilyloxyvaleraldehyde in 25 mL of dry CH₂Cl₂ Stirring was continued overnight (16 h) at 20° C. The solvent was removed under vacuum (aspirator) and the residue taken up in CHCl₃ (150 mL). To this yellow solution was added 2.5 mL of benzyl bromide and the mixture heated at reflux for 18 h. The solvent was removed under vacuum (aspirator) and the residue triturated with pentane to give a gummy solid. The pentane was removed by pipette and the gum triturated twice more with additional pentane. To this residue was added 100 mL of dry methanol and 6 mL 4 eq; 0.043 mol) of dry triethylamine and the whole heated at reflux for 3 h. After cooling, the solvent was removed under vacuum (aspirator) and the residue taken up in CH₂Cl₂ and washed with 10% Na₂CO₃. After drying over MgSO₄ and concentration under vacuum (aspirator), the residue was adsorbed on silica gel (20 g) and applied to the top of a silica gel column (200 g, as a slurry in ethyl ether/pentane 3:7). Elution with the latter solvent mixture afforded 5.6 g (70% overall based on the azepine) of the title compound. TLC: (Silica) R$_f$ 0.60 (ethyl ether), detection, CAS, dark blue green with yellow center.

EXAMPLE 53

Methyl 3-Benzyl-1.2,3,3a,4,5-hexahydro-4-(2.2-dimethyl-3-hydroxypropyl)-7H-pyrrolo (2,3-d) carbazole-6-carboxylate To a solution of 873 mg (1.56 mmol) of methyl 3-benzyl-1,2,3,3a,4,5-hexahydro-4-[2,2-dimethyl-3-(t-butyldimethylsilyloxy)propyl]-7H-pyrrolo(2,3-d)carbazole-6-carboxylate in 30.5 mL of THF and 15 mL of water was added 5.24 g (20 eq) of p-toluenesulfonic acid. The reaction mixture was stirred for 90 min. at 20° C. and saturated aqueous K₂CO₃ solution was added until a pH=9–10 was obtained. Ethyl ether (100 mL) was added and the two layers were separated. The aqueous layer was extracted once with 100 mL of ethyl ether and twice with 100 mL of CH₂Cl₂. The combined organic layers were dried over MgSO₄ and the solvents evaporated in vacuo (aspirator). The crude product was purified by column chromatography on silica gel (40 g). Elution with CH₂Cl₂ followed by ethyl ether gave 0.678 g (97.5%) of the title compound as a white foam. TLC: (Silica) R$_f$0.50 (ethyl ether), detection with CAS (blue with developing yellow center), UV (long and short wave length).

EXAMPLE 54

Methyl 3-Benzyl-1.2,3.3a.4.5-hexahydro-4-[2.2-dimethyl-3-(p-toluenesulfonyloxy)propyl]-7H-pyrrolo(2,3-d)carbazole-6-carboxylate To a solution of 669 mg (1.11 mmol) of methyl 3-benzyl-1,2,3,3a,4,5-hexahydro-4-[2,2-dimethyl-3-(t-butyldimethylsilyloxy)propyl]-7H-pyrrolo(2,3-d)carbazole-6-carboxylate in 60 mL of dry CH₂Cl₂ containing 0.777 mL (3.3 eq; 4.44 mmol) of diisopropyl ethylamine was added portion wise, over 1 h, 1.315 g (3 eq; 4.03 mmol) of p-toluenesulfonic anhydride. When the addition was completed, 16.4 mg (0.1 eq; 0.134 mmol) of 4-dimethylaminopyridine was added all at once and the reaction mixture stirred for 3 h at 20° C.; after this time, 0.777 mL of diethylamine was added, followed by 1.315 g of p-toluenesulfonic anhydride, added portion-wise over 15–20 min. and the whole was stirred for 24 h. The solvent was removed under vacuum and the residue purified by column chromatography over silica gel (120 g). Elution with CH₂Cl₂, followed by CH₂Cl₂/ethyl ether 4:1, afforded 580 mg (72%) of the title compound. TLC: (Silica) R$_f$0.52 (CH₂Cl₂/ethyl ether, 9:1), detection: CAS (blue with yellow center, then orange).

EXAMPLE 55

7S and 7R 5,7-PARF Methyl 3-Benzyl-1,2,3,4,5,6,7,8-octahydro-5-[2,2-dimethyl-3-(p-toluenesulfonyloxy)propyl]-azonino (6,7-b)indole-7-(15-vindolinyl)-7-carboxylate To a solution of 669 mg (1.11 mmol) of methyl 3-benzyl-1,2,3,3a,4,5-hexahydro-4-[2,2-dimethyl-3-(p-toluenesulfonyloxy)propyl]-7H-pyrrolo(2,3-d)carbazole-6-carboxylate dissolved in 60 mL of dry CH₂Cl₂ and cooled to 0° C. (ice-H₂O) was added 0.195 mL (1.41 mmol 1.3 eq) of triethylamine, followed after 5 min. by 0.253 mL (1.3 eq; 1.41 mmol) of t-butyl hypochlorite. The reaction mixture was stirred for 15 min. at 0° C. and cold water (20 mL) was added. The two layers were separated and the aqueous layer extracted with 20 mL of CH₂Cl₂. The combined organic layers were dried over MgSO₄ and the solvent removed under aspirator vacuum to yield the chlorination product as a yellow foam. TLC: (Silica) $R_f$=0.64 (ethyl ether) detection: CAS (rust brown). The chlorination product was dissolved in 60 mL of dry acetone and cooled at 0° C. (ice-water) and to the cold solution was added 457 mg (0.9 eq; 1.00 mmoles) of vindoline base, followed by 0.493 mL (3 eq; 3.345 mmol) of fluoroboric acid etherate. After stirring for 5 min. (651 mg (3 eq; 3.34 mmol) of AgBF₄ was added, all at once, in the dark. The reaction mixture immediately became heterogeneous and stirring was continued at 0° C. for 30 min. Quenching was effected by adding a solution of 10% NH₄OH saturated with NaCl (pH=10-12). Addition of dichloromethane, separation of the layers and extraction of the aqueous layer three times with 60-70 mL of CH₂Cl₂, drying over MgSO₄ and removal of the solvents under aspirator gave a crude product (orange foam) which was used as such in the next step. To the crude product, dissolved at 20° C. in 70 mL of dry acetic acid, was added portion wise over 20-30 min. 615 mg (10 eq: 11.1 mmoles) of KBH₄. After addition was completed, stirring was continued for a further 10 min. then the homogeneous reaction mixture was slowly added to 400 mL of a mixture of 37% NH₄OH and crushed ice. The solution was made strongly basic (pH=10-12) by adding more NH₄OH, if necessary. Extraction with CH₂Cl₂, drying over MgSO₄ and concentration under aspirator vacuum gave a product which was purified by flash column chromatography. (4.5×11 cm, silica gel, elution with ethyl acetate). Three fractions were obtained: Fraction 1: contained the 7S isomer of the title oompound, fraction 2: contained a mixture of the 7R and 7S isomers, fraction 3: contained about 200 mg of the 7R isomer and about 120 mg of vindoline as judged by NMR. Fraction 1+fraction 2: 650 mgr. Total eluate 970 mg. TLC: (Silica gel, ethyl acetate) Rf 7S isomer 0.35 (CAS grey-brown), $R_f$ 7R isomer 0.27 (CAS grey-brown), Rf vindoline 0.21 (CAS purple).

EXAMPLE 56

4′-Deoxy-4′-deethyl -4′,4′-dimethylvinblastine (2′S, 18′S) and its 2′R, 18′R Diastereoisomer To the combined three fractions of 7S and 7R 5,7-PARF methyl 3-benzyl-1,2,3,4,5,6,7,8-octahydro-5-(2,2-dimethyl-3-(p-toluenesulfonyloxy)propyl)-azonino (6,7-b)indole-7-(15-vindolinyl)-7-carboxylate and vindoline (970 mg) was added 150 mL of dry toluene and the clear solution was heated at reflux (bath Temperature=120° C.) for 5 days, under an argon atmosphere. The solution was cooled and the toluene removed first under aspirator and finally at 0.01 Torr to give a yellow-orange solid. Ethyl ether was added and the solid scratched vigorously. The ether was removed by using a pipette, or by filtration, and the previous operation repeated three more times to give a faint yellow solid. 500 mg, 57.5%). The solid was dissolved in 50 mL of dry methanol and 100 mg of 5% Pd on carbon added under argon. This mixture was submitted to hydrogenation under 1 atom of hydrogen at 20° C. After 4 h, the catalyst was removed by filtration through a pad of Celite 545 and washed well with additional methanol (50–60 mL) and CH₂Cl₂ (100 mL). The solvents were removed under aspirator vacuum and the glassy solid taken up in CH₂Cl₂ and treated with 10% Na₂CO₃ until basic (pH=10-11). Separation of the two layers, extraction of the aqueous layer (three times with CH drying of the combined organic layers over MgSO₄ and removal of the solvent under aspirator vacuum gave a product which was purified by column chromatography over silica gel (15 g) using as eluant ethyl acetate/tthanol 85:15, followed by ethyl acetate/ethanol, 7:3. Thus 90 mg of the 18′R isomer of the title compounds, followed by 96 mg of the 18′S isomer was obtained (49% yield). TLC: (Silica gel, ethyl acetate/ethanol, 85:15) Rf 0.32 for 18′R isomer and $R_f$ 0.09 for 18′S isomer (CAS brown).

EXAMPLE 57

2R 2-Ethyl-2,3-epoxypropanol

Dichloromethane (80 mL) and powdered activated 4.0 A molecular sieves (2.0 g, Aldrich) were stirred in a 3-neck flask equipped with a thermometer, a dropping funnel and a septum and cooled to −5° C. D(−) Diethyltartrate (0.80 g, 3.9 mmol) and titanium (IV) isopropoxide (0.73 g, 2.6 mmol) were added sequentially. The reaction was then brought to −20° C. (dry ice, carbon-tetrachloride) and t-butyl hydroperoxide (18.57 mL, 78 mmol, 4.2 M in toluene) was added, the mixture stirred for 10 minutes and 2-ethyl allyl alcohol (4.48 g, 52 mmol in 3 mL of dichloromethane) was added dropwise with vigorous stirring over 10 minutes.

The reaction mixture was stirred for 60 minutes at −20° to 0° C., then quenched with water (14 mL), allowed to warm to room temperature, and stirred another 60 minutes. The tartrate was hydrolyzed by addition of 3.5 mL of a 30% aqueous solution of sodium hydroxide saturated with sodium chloride and stirring for 30 min. The mixture was filtered through a glass wool plug, the organic layer was separated and the aqueous phase was extracted with dichloromethane (2×15 mL). The combined organic layers were dried over magnesium sulfate and filtered through Celite. Concentration and distillation gave the title compound as a clear colorless oil (3.03 g, 57%, bp 62° C./7-10 mm). TLC $R_f$ 0.24 (silica gel, 1:1 ether:hexane, CAS char:tan).

EXAMPLE 58

2S 2-Ethyl-2-hydroxyhex-5-enol

A mixture of 2 R 2-ethyl-2,3-epoxypropanol (2.6 g, 25.5 mmol) and copper iodide (475 mg, 2.5 mmol) was stirred in tetrahydrofuran (50 mL) under nitrogen and brought to −30° C. (dry ice, acetonitrile). Vinyl magnesium bromide [32 mL, 2 M in tetrahydrofuran (THF), 2.5 eq] was added from a dropping funnel at such a rate as to maintain the temperature at −25 to −30° C. The reaction mixture was stirred at −30° C. for 2 h then brought to 0° C. and acidified with 10% HCl. The THF layer was separated and the aqueous phase was extracted with ether (3×50 mL). The organic layers were combined, dried over sodium sulfate, oncentrated and distilled to give the title compound as a clear colorless oil (2.2 g, 60%, b.p. 85° C./5 mm). TLC $R_f$ 0.26 (silica gel, 5% MeOH in CH₂Cl₂, CAS/char:brown).

EXAMPLE 59

2S 2-Ethyl-2-hydroxyhex-5-enol Acetonide

A solution of 2S 2-ethyl-2-hydroxyhex-5-enol (1.7 g, 11.8 mmol) in acetone (25 mL) was stirred under nitrogen with 2,2-dimethoxypropane (2 mL) and a catalytic amount of p-toluene sulfonic acid. After 2 h, the reaction was complete as indicated by TLC. The acetone was removed under reduced pressure at room temperature, the residue was basified with aqueous saturated sodium bicarbonate and extracted with ether (3×50 mL). The combined ether layers were dried over sodium sulfate. Concentration and distillation (75°-80° C., 10 mm) gave 1.5 g of the title product (70%). TLC $R_f$ 0.72 (silica gel, 4:1 hexane-ether).

EXAMPLE 60

4S 4-Ethyl-4,5-dihydroxypentanal Acetonide

A solution of 2S 2-ethyl-2-hydroxyhex-5-enol acetonide (1.2 g, 6.52 mmol) in dichloromethane (25 mL) was brought to −78° C. (dry ice, acetone) and ozone was bubbled through until the reaction mixture turned a pale blue (approx 15 min.) The reaction mixture was then flushed with nitrogen for 1 h, triphenylphophine (850 mg, 3.26 mmole) was added and the mixture was allowed to slowly warm to room temperature. The solvent was removed under reduced pressure and the residue was taken up in hexane, filtered and again concentrated. Flash chromatography on 50 g of silica gel, eluting with 3:2 hexane/ether, gave 0.92 g (76%) of the title aldehyde. TLC $R_f$ 0.39 (silica gel, 3:2 hexane-ether).

EXAMPLE 61

3aR,4R and 3aS.4R 2'S-Methyl 3-Benzyl-1,2,3,3a,4,5-hexahydro-4-(2-ethyl-2,3-acetonidopropyl)-7H-pyrrolo (2,3-d)carbazole-6-carboxylate A solution of 500 mg (2.05 mmol) of 1,2,3,4,5,6-hexahydroazepino-[4,5-b] indole-5-carboxylate and 420 mg (2.25 mmol, 1.1 eq) of 4S 4-ethyl-4,5-dihydroxypentanal acetonide in 50 mL of tetrahydrofuran was heated at reflux under nitrogen until TLC showed no remaining starting material (approx. 2 h). The solvent was removed under reduced pressure and the residue was taken up in 50 mL of toluene. Any water present was azeotroped off and 0.50 mL (4.2 mmol, 2 eq.) of benzyl bromide was added. The reaction mixture was heated at reflux for 17 hours. Concentration under vacuum and flash chromatography of the residue on a 23×3.5 cm silica column, eluting with 3:2 hexane/ether, gave 730 mg of the title products (71% yield). TLC $R_f$ 0 32 (silica gel, 1:1, ether:hexane, CAS-blue).

EXAMPLE 62

3aR.4S and 3aS.4R 2'S Methyl 3-Benzyl-1.2,3,3a,4,5-hexahydro-4-(2-ethyl-2,3-dihydroxypropyl)-7H-pyrrolo (2,3-d) carbazole-6-carboxylate The mixture of the title compounds' acetonide (500 mg, 1.0 mmol) was heated at reflux in 25 mL of methanol containing 10 mL of 10 aqueous hydrochloric acid for 15 min. The methanol was removed under reduced pressure, the solution basified with ammonium hydroxide and then extracted with ether (3×50 mL). Concentration gave 440 mg (95%) of the title diols. Separation of the diasteromers (400 mg) was partially effected by flash chromatography on a 5×12 cm silica gel column eluting with 0.2% triethylamine in ether, to give 175 mg of the less polar 3aS,4R title isomer, TLC $R_f$0.32 (silica gel, ether, CAS-blue). This was followed by the more polar 3aR,4S title isomer; TLC $R_f$0.25 (silica gel, ether, CAS blue-fade to purple), and 110 mg of a mixture of the two isomrs.

EXAMPLE 63

3aR,4S,2'S Methyl 3-Benzyl-1,2,3,3a,4,5-hexahydro4-(2-ethyl-2-hydroxy-3-p-toluenesulfonyloxypropyl)-7H-pyrrolo(2,3-d)carbazole-6-carboxylate A solution of 175 mg (0.38 mmol) of 3aR,4S,2'S mehhyl 3-benzyl-1,2,3,3a,4,5-hexahydro-4-(2-ethyl-2,3-dihydroxypropyl)-7H-pyrrolo (2,3-d)carbazole-6-carboxylate and 106 μL (0.76 mmol) of triethylamine in 25 mL of dichloromethane was brought to 0° C. and 247 mg (0.76 mmol) of p-toluene sulfonic anhydride was added. The reaction flask was purged with nitrogen and the reaction mixture stirred for 26 h. The reaction mixture was then washed with water, dried over magnesium sulfate and concentrated under reduced pressure. Flash chromatography on a 15×3.5cm silica gel column gave 177 mg (76%) of the title tosylate. TLC $R_f$ 0.45 (silica gel, 4:1 ether-hexane, CAS-blue).

EXAMPLE 64

3aR,4S,2'S Methyl 3-Benzyl-1.2,3,3a,4,5-hexahydro-4-(2-ethyl-2-trimethylsilyloxy-3-p-toluenesulfonyloxypropyl)-7H-pyrrolo(2,3-d)carbazole-6-carboxylate A solution of 150 mg (0.32 mmol) of 3aR,4S 2'S methyl 3-benzyl-1,2,3,3a,4,5-hexahydro-4-(2-ethyl-2-hydroxy-3-p-toluenesulfonyloxy propyl)-7H-pyrrolo(2,3-d) carbazole-6-carboxylate and 64 mL (1.5 eq) of diisopropylethyl amine in 25 mL of tetrahydrofuran was stirred under nitrogen and brought to 0° C. and 71 μL (1.5 eq) of trimethylsilyl trifluoromethanesulfonate added by syringe. The solution was stirred for 15 min, then washed with 15 mL of aqueous saturated sodium bicarbonate, dried over magnesium sulfate and concentrated under reduced pressure. Flash chromatography on a 12.5×3.5 cm silica gel column, eluting with 1:1 ether-hexane, gave 154 mg (92%) of the title product as a white foam. TLC $R_f$0.37 (silica gel, 1:1 ether-hexane, CAS-blue green).

EXAMPLE 65

7S,4S,2'S Methyl 3-Benzyl-1,2,3,4,5,6,7,8-octahydro-5-(2-ethyl-2-trimethylsilyloxy-3-p-toluenesulfonyloxypropyl) azonino (6.7-b)indole-7-(15-vindolinyl)-7-carboxylate A solution of 0.10 g (0.14 mmol) of 3aR,4S,2'S methyl 3-benzyl-1,2,3,3a,4,5-hexahydro-4-(2-ethyl-2-trimethylsilyloxy-3-p-toluenesulfonyloxypropyl)-7H-pyrrolo(2,3-d)carbazole-6-carboxylate and 21 μL (1.1 eq) of triethylamine in 5 mL of dichloromethane was stirred under nitrogen and brought to 0° C. Dropwise addition of 19 μL (1.1 eq) of t-butyl hypochlorite in 2 mL dichloromethane and stirring for 5 min gave a solution which, by TLC, was free of starting compound (CAS, blue) and which contained a new, less polar chlorination product ($R_f$ 0.6, 2:3 hexane/ether, CAS, purple). The solution was washed with 2×5 mL of water, dried over magnesium sulfate and concentrated under vacuum to give a white foam which was used in the next reaction. To a solution of the chlorination product and 0.063 g (0.95 eq.) of vindoline in 5 mL of dry acetone, was added 47 μL (2 eql,of tetrafluoroboric acid-diethyl ether complex. After 5 min. 0.056 g (2 eq) of silver tetrafluoroborate in 2 mL of dry acetone was added, causing the mixture to become heterogeneous. After 5 min, TLC showed no remaining starting material. Addition of 10 mL of 10% aqueous ammonium hydroxide, extraction with 4 x 15 mL of dichloromethane, drying (MgSO₄) and concentration under vacuum gave a white foam.

This material was dissolved in 10 mL of acetic acid and, with stirring, 0.078 g (10 eq) of potassium borohydride was slowly added. After stirring for 10 min, the reaction mixture was poured onto ice and made strongly basic with concentrated ammonium hydroxide. Extraction with 4×15 mL of dichloromethane, drying (MgSO₄) and concentration under vacuum gave a white foam. Flash chromatography on silica, eluting with ethyl acetate gave 0.126 g (80% based on vindoline) of the title product. TLC R$_f$ 0.61 (ethyl acetate, CAS, dark brown-purple).

EXAMPLE 66

7S,4S,2′S Methyl 3-Benzyl-1,2,3,4,5,6,7,8-octahydro-5-(2-ethyl,2,3-oxopropyl)azonino(6,7-b)indole-7-(15-vindolinyl)-7-carboxylate To a solution of 0.07 g (0.06 mmol) of 7S,4S,2′S methyl 3-benzyl-1,2,3,4,5,6,7,8-octahydro-5-( 2-ethyl-2-trimethylsilyloxy-3-p-toluenesulfonyloxypropyl) azonino (6,7-b)indole-7-(15-vindolinyl)-7-carboxylate in 20 mL of tetrahydrofuran, was added 0.184 mL (3 eq in 1 M THF) of tetrabutyl ammonium fluoride. After 25 min, TLC showed complete conversion of starting material to a more polar product. The reaction mixture was washed with aqueous saturated sodium bicarbonate, dried (MgSO₄) and concentrated under vacuum. Flash chromatography on silica, eluting with ethyl acetate, gave 0.047 g (85% yield) of the title compound. TLC R$_f$ 0.33 (silica gel, ethyl acetate, CAS-brown).

EXAMPLE 67

Vinblastine and its 1′-Axial Conformaional Isomer

A solution of 0.040 g (0.044 mmol) of 7S,4S,2′S methyl 3-benzyl-1,2,3,4,5,6,7,8-octahydro-5-(2-ethyl,2,3-oxopropyl) azonino(6,7-b)indole-7-(15-vindolinyl)-7-carboxylate in 10 mL of methanol was heated at reflux for 26 h at which time TLC showed no remaining starting material and a new more polar product (R$_f$ 0.20, 2% triethylamine-methanol CAS-blue). The reaction mixture was cooled and flushed with nitrogen and 20 mg of 5% Pd on charcoal was added. The reaction mixture was stirred under a hydrogen atmosphere at room temperature for 2 h, filtered, and concentrated under vacuum. Flash chromatography on a 22×12 cm silica gel column, eluting with 1% triethylamine in methanol gave 0.032 g (89%) of the 1′ equatorial conformational isomer of vinblastine as a white solid. TLC R$_f$ 0.23 (silica gel, 1% triethylamine in methanol, CAS purple).

This product was dissolved in toluene and heated at reflux for 8 h, at which time TLC showed no remaining starting material and a new less polar product, which chromatographically matched an authentic sample of vinblastine, TLC R$_f$ 0.24 (silica gel, 5% methanol in dichloromethane, CAS purple). Concentration of the solvent and flash chromatography, eluting with 5:1:0.01 ether-acetone-triethylamine, gave 0.03 g (95% yield) of vinblastine.

EXAMPLE 68

Vinblastine

A solution of 0.010 g (0.0087 mmol) of 7S,4S,2′S methyl 3-benzyl-1,2,3,4,5,6,7,8-octahydro-5-(2-ethyl-2-trimethylsilyloxy-3-p-toluenesulfonyloxypropyl) azonino(6,7-b)indole-7-(15-vindolinyl)-7-carboxylate in 5 mL of methanol was heated at reflux under nitrogen for 40 h, at which time TLC showed no remaining starting material and a new, more polar product (R$_f$ 0.38, 2% triethylamine in methanol, CAS-brown). The reaction mixture was cooled to room temperature, flushed with nitrogen and 0.010 g of 10% palladium on carbon was added. The mixture was stirred under a hydrogen atmosphere for 2 h. TLC then showed complete conversion of starting material to a less polar compound (TLC, R$_f$ 0.36, 5% methanol in dichloromethane, CAS-purple). The reaction mixture was filtered, the filtrate washed with dichloromethane and the combined solvents were concentrated under vacuum. The concentrate was dissolved in 5 mL of tetrahydrofuran and 26 μL of tetrabutyl ammonium fluoride (1 M in THF, 3 eq) was added. After 30 min TLC showed no remaining starting material and only the presence of vinblastine in its natural conformation.

I claim:

1. A process for producing a compound of the formula:

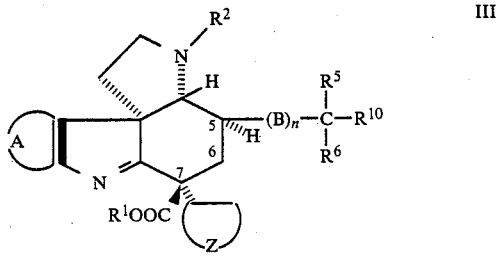

wherein n is an integer from 0 to 1; Z is the remaining portion of a ring selected from the group consisting of vindoline, 16-lower alkoxy vindoline, des(N-methyl)-N-formyl vindoline, des(N-methyl)-N-formyl-16-lower alkoxy vindoline and 16-methoxy-2,3-dihydro N$^a$ methyl-tabersonine; R$^1$ is lower alkyl; R$^2$ is an amino protecting group; R$^{10}$ is —CH$_2$Y, formyl or formyl protected through the formation of an acetal; A is the remaining portion of a benzene ring; B is an alkylene chain of 1 to 4 carbon atoms; Y is individually a leaving group or a hydrolyzable ether group, R$^5$ is hydrogen or lower alkyl, R$^6$ is individually hydrogen, lower alkyl, or taken together with Y forms a lower alkylidenedioxy or oxo or mixtures thereof with the corresponding 7R-diastereomer having the configuration at C-5 opposite to that shown above, comprising condensing a compound of the formula

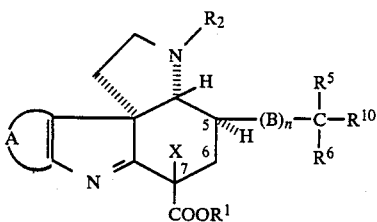

wherein n, $R^1$, $R^2$, $R^5$, $R^6$, A, $R^{10}$ and B are as above and X is halogen with the proviso that when $R^6$ is a hydrolyzable ether group, $R^{10}$ is —$CH_2Y$, Y is a leaving group;

with vindoline, 16-lower alkoxy vindoline, des(N-methyl)-N-formyl vindoline, des(N-methyl)-N-formyl-16-lower alkoxy vindoline or 16-methoxy-2,3-dihydro $N^a$ methyl-tabersonine or a salt thereof.

2. The process of claim 1 wherein B is methylene and n is 1.

3. The process of claim 1 wherein $R^6$ is hydrogen, lower alkyl or taken together with Y forms a lower alkylidenedioxy.

4. The process of claim 3 wherein n is 1 and B is a methylene.

5. The process of claim 1 wherein the condensation is carried out in the presence of a silver salt.

6. The process of claim 1 wherein the compound containing the vindoline ring system is vindoline.

7. A process for producing a compound of the formula:

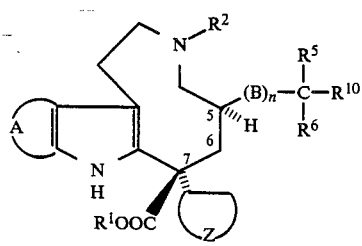

wherein n is an integer from 0 to 1; Z is the remaining portion of a ring selected from the group consisting of vindoline, 16-lower alkoxy vindoline, des(N-methyl)-N-formyl vindoline, des(N-methyl)-N-formyl-16-lower alkoxy vindoline and 16-methoxy-2,3-dihydro $N^a$ methyl-tabersonine; $R^1$ is lower alkyl; $R^2$ is an amino protecting group; $R^{10}$ is —$CH_2$ Y, formyl or formyl protected through the formation of an acetal; A is the remaining portion of a benzene ring; B is an alkylene chain of 1 to 4 carbon atoms; Y is individually a leaving group or a hydrolyzable ether group, $R^5$ is hydrogen or lower alkyl , $R^6$ is individually hydrogen lower alkyl, or taken together with Y forms a lower alkylidenedioxy or oxo;

or mixtures thereof with the corresponding 7R-diastereomer having a configuration at C-5 opposite to that shown, comprising condensing a compound of the formula

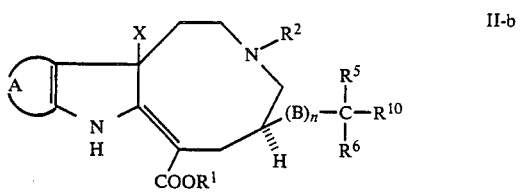

wherein n, $R^1$, $R^2$, $R^5$, $R^6$, A, $R^{10}$ and B are as above and X is hydrogen or oxo;

with vindoline, 16-lower alkoxy vindoline, des(N-methyl)-N-formyl vindoline, des(N-methyl)-N-formyl-16-lower alkoxy vindoline, 16-methoxy-2,3-dihydro $N^a$ methyl-tabersonine or a salt thereof.

8. The process of claim 7 wherein n is 1 and B is methylene.

9. The process of claim 7 wherein $R^6$ is hydrogen, lower alkyl or taken together with Y forms a lower alkylidenedioxy and X is halogen.

10. The process of claim 9 wherein n is 1 and B is a methylene.

11. The process of claim 7 wherein said condensation is carried out in the presence of a silver salt.

12. A compound of the formula

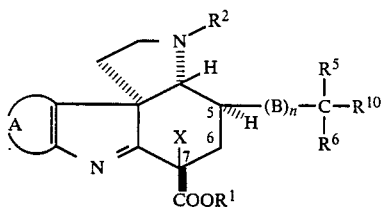

wherein n is an integer from 0 to 1, $R^1$ is lower alkyl; $R^2$ is an amino protecting group; $R^{10}$ is —$CH_2$ Y, formyl or formyl protected through the formation of an acetal; A is the remaining portion of a benzene ring; B is an alkylene chain of 1 to 4 carbon atoms, Y is individually a leaving group or a hydrolyzable ether group; X is halogen; $R^5$ is hydrogen or lower alkyl; and $R^6$ is individually hydrogen; lower alkyl; or taken together with Y forms a lower alkylidenedioxy; or oxo.

13. The compound of claim 12 wherein $R^6$ is hydrogen, lower alkyl, or taken together with Y forms lower alkylidenedioxy.

14. The compound of claim 13 wherein B is methylene, and n is 1.

15. The compound of claim 14 wherein $R^6$ taken together with Y forms lower alklidenedioxy.

16. The compound of claim 14 wherein said compound is methyl 3-benzyl-6-chloro-1,2,3,3a,4,5-hexahydro-4(3-p-toluenesulfonyloxpropyl)-pyrrolo(2,3-d)carbazole-6-carboxylate.

17. A compound of the formula

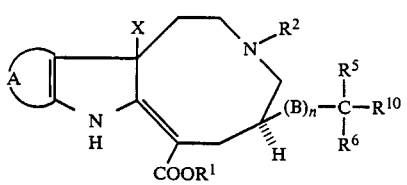

wherein n is an integer of from 0 to 1; $R^1$ is lower alkyl; $R^2$ is an amino protecting group; $R^{10}$ is —$CH_2$ Y, formyl or formyl protected through the formation of an acetal; A is the remaining portion of a benzene ring; B is an alkylene chain of 1 to 4 carbon atoms; Y is individually a leaving group or a hydrolyzable ether group; X is halogen; $R^5$ is hydrogen or lower alkyl; and $R^6$ is individually hydrogen or lower alkyl or taken together with Y forms a lower alkylidenedioxy or oxo.

18. The compound of claim 17 wherein $R^6$ is hydrogen, lower alkyl or taken together with Y form a lower alkylidenedioxy.

19. The compound of claim 18 wherein B is methylene and n is 1.

20. The compound of claim 19 wherein said compound is methyl-3-benzyl-12b-chloro-1,2,3,4,5,6-hexahydro-5(3-p-toluenesulfonyloxypropyl) azonino (6,7-b)-2,3-dihydroindole-7-carboxylate.

21. A compound of the formula

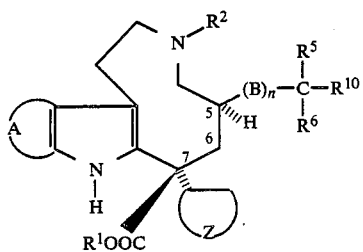

V wherein n is an integer from 0 to 1; Z is the remaining portion of a ring selected from the group consisting of vindoline, 16-lower alkoxy vindoline, des(N-methyl)-N-formyl vindoline, des(N-methyl)-N-formyl-16-lower alkoxy vindoline and 16-methoxy-2,3-dihydro $N^a$ methyl-tabersonine; $R^1$ is lower alkyl; $R^2$ is an amino protecting group; $R^{10}$ is —$CH_2$ Y, formyl or formyl protected through the formation of an acetal; A is the remaining portion of a benzene ring; B is a alkylene chain of 1 to 4 carbon atoms; Y is individually a leaving group or a hydrolyzable ether group, $R^5$ is hydrogen or lower alkyl, $R^6$ is individually hydrogen, lower alkyl, or taken together with Y forms a lower alkylidenedioxy or oxo;

or mixtures thereof with the corresponding 7R diastereomer having the configuration at C-5 opposite to that shown above.

22. The compound of claim 21 wherein B is methylene and n is 1.

23. The compound of claim 21 wherein $R^6$ is hydrogen, lower alkyl or taken together with Y forms lower alkylidenedioxy.

24. The compound of claim 23 wherein B is methylene and n is 1.

25. The compound of claim 22 wherein said compound is 5,7-priority anti-reflective (PARF) methyl 3-benzyl-1,2,3,4,5,6,7,8-octahydro-5-(3-p-toluenesulfonyloxypropyl)azonino (6,7-b) indole-7-(15-vindolinyl)-7-carboxylate.

26. A compound of the formula:

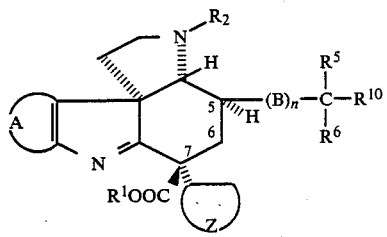

III wherein n is an integer from 0 to 1; Z is the remaining portion of a ring selected from the group consisting of vindoline; 16-lower alkoxy vindoline, des(N-methyl)-N-formyl vindoline, des(N-methyl)-N-formyl-16-lower alkoxy vindoline and 16-methoxy-2,3-dihydro $N^a$ methyl-tabersonine; $R^1$ is lower alkyl; $R^2$ is an amino protecting group; $R^{10}$ is —$CH_2$ Y, formyl or formyl protected through the formation of an acetal; A is the remaining portion of a benzene ring; B is an alkylene chain of 1 to 4 carbon atoms; Y is individually a leaving group or a hydrolyzable ether group; $R^5$ is hydrogen or lower alkyl, $R^6$ is individually hydrogen lower alkyl, or taken together with Y forms a lower alkylidenedioxy or oxo;

or mixtures thereof with the corresponding 7R diastereomer having the configuration at C-5 opposite to that shown.

27. The compound of claim 26 wherein B is methylene and n is 1.

28. The compound of claim 26 wherein $R^6$ is hydrogen, lower alkyl or taken together with Y forms a lower alkylidenedioxy.

29. The compound of claim 28 wherein B is methylene and n is 1.

30. The compound of claim 27 wherein said compound is the 4,6-priority anti-reflective (PARF) methyl 3-benzyl-1,2,3,3a,4,5-hexahydro-4(3-p-toluenesulfonyloxypropyl)-6-(15-vindolinyl)pyrrolo(2,3-d)carbazole-6-carboxylate.

31. A compound of the formula

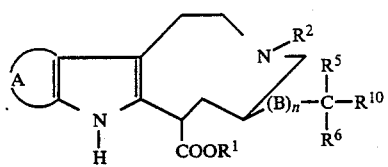

XIX wherein n is an integer of from 0 to 1; A is the remaining portion of a benzene ring; B is an alkylene chain of from 1 to 4 carbon atoms; $R^1$ is lower alkyl; $R^{10}$ is —$CH_2$ Y, formyl or formyl protected through the formation of an acetal; Y individually forms a leaving group or a hydrolyzable ether group; $R^2$ is an amino protecting group; $R^5$ is hydrogen or lower alkyl; $R^6$ is individually hydrogen, lower alkyl or taken together with Y forms a lower alkylidenedioxy or oxo.

32. The compound of claim 31 wherein Y is tosyloxy, and B is methylene.

33. The compound of claim 32 wherein said compound is methyl 3-benzyl-1,2,3,4,5,6,7,8-octahydro-5(3-p-toluenesulfonyloxypropyl)azonino (6,7-b)indole-7-carboxylate.

34. A compound of the formula:

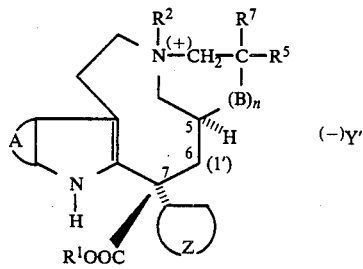

wherein n is an integer of from 0 to 1; A is the remaining portion of a benzene ring; B is an alkylene chain of from 1 to 4 carbon atoms; $R^1$ is lower alkyl; Y' is an anion; $R^2$ is an amino protecting group; $R^5$ is hydrogen or lower alkyl; $R^7$ is hydrogen, hydroxy, hydrolyzable ether group or lower alkyl and Z is the remaining portion of a ring selected from the group consisting of vindoline, 16-lower alkoxy vindoline, des(N-methyl)-N-formyl vindoline, des(N-methyl)-N-formyl-16-lower alkoxy vindoline or 16-methoxy-2,3-dihydro $N^a$ methyl-tabersonine; with the proviso that when n is 1, B is methylene, and one of $R^5$ or $R^7$ is ethyl; the other of said $R^5$ or $R^7$ is lower alkyl, or mixtures thereof with the corresponding 7R-diastereomer having the configuration at C-5 opposite to that shown above.

35. The compound of claim 34, wherein n is 1, and B is methylene.

36. The compound of claim 34 wherein $R^7$ is hydrogen or lower alkyl.

37. The compound of claim 36 wherein n is 1 and B is methylene.

38. The compound of claim 35 wherein said compound is 6'-benzyl-4'-deethyl-4'-deoxy-vinblastinonium tosylate.

39. The compound of claim 38, wherein said compound has the structure of a 1' equatorial piperidine ring conformational isomer.

40. The salt of 4'-deoxy-vinblastine having the nitrogen at the 6' position quaternarized with an amino protecting group, said salt having the structure of a 1' equatorial piperidine ring conformational isomer.

41. The salt of claim 40, where said salt is 6'-benzyl-4'-deoxy vinblastoninonium tosylate.

42. A process of producing a compound of the formula:

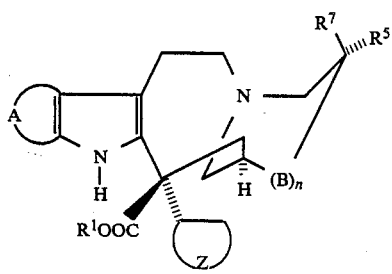

wherein n is an integer of from 0 to 1; Z is the remaining portion of a ring selected from the group consisting of vindoline, 16-lower alkoxy vindoline, des(N-methyl)-N-formyl vindoline, des(N-methyl)-N-formyl-16-lower alkoxy vindoline and 16-methoxy-2,3-dihydro $N^a$ methyl-tabersonine; $R^1$ is lower alkyl; A is the remainder of a benzene ring, B is an alkylene chain of 1 to 4 carbon atoms; $R^5$ is hydrogen or lower alkyl; and $R^7$ is lower alkyl, hydrogen or hydroxy;

comprising isomerizing a compound of the formula:

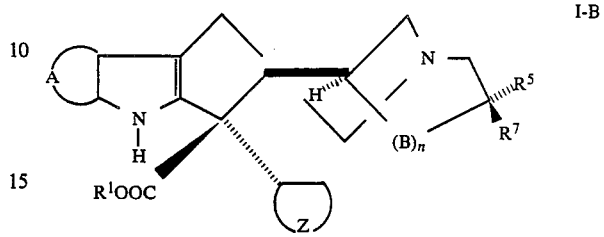

wherein n, $R^1$, $R^5$, $R^7$, A, B and Z are as above; by heating.

43. The process of claim 42 wherein said is heating carried out in a hydrocarbon solvent.

44. The process of claim 43 wherein the heating is carried out at a temperature of from 30° C. to the reflux temperature of the solvent.

45. A compound of the formula:

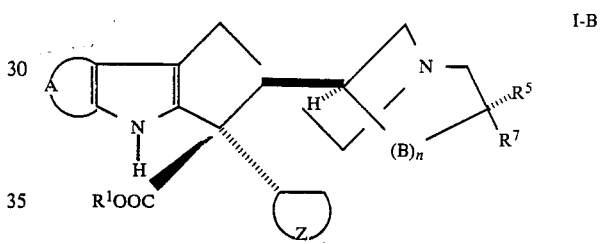

wherein n is an integer of from 0 to 1; Z is the remaining portion of a ring selected from the group consisting of vindoline, 16-lower alkoxy vindoline, des(N-methyl)-N-formyl vindoline, des(N-methyl)-N-formyl-16-lower alkoxy vindoline and 16-methoxy-2,3-dihydro $N^a$ methyl-tabersonine; $R^1$ is lower alkyl; A is the remaining portion of a benzene ring; B is an alkylene chain of from 1 to 4 carbon atoms, $R^5$ is hydrogen or lower alkyl; and $R^7$ is hydrogen, hydroxy or lower alkyl;

or pharmaceutically acceptable salts thereof.

46. The compound of claim 45 wherein Z is vindoline, n is 1, and B is methylene.

47. A compound of the formula:

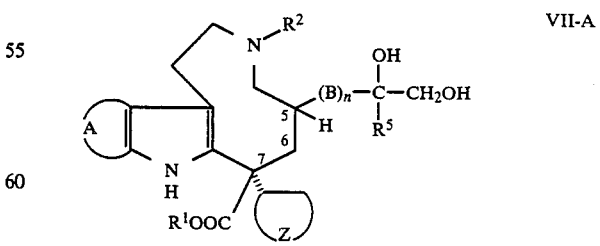

wherein n is an integer of from 0 to 1; Z is the remaining portion of a ring selected from the group consisting of vindoline, 16-lower alkoxy vindoline, des(N-methyl)-N-formyl vindoline, des(N-methyl)-N-formyl-16-lower alkoxy vindoline and 16- methoxy-2,3-dihydro $N^a$ methyl-tabersonine; A is the remainder of a benzene ring; $R_2$ is hydrogen or an amino protecting group; B is an alkylene chain of 1 to 4 carbon chains, $R_5$ is hydrogen or lower alkyl;

or mixtures thereof with its corresponding 7R diastereomer having a configuration at C-5 opposite from that shown.

48. The compound of claim 47 where B is methylene and n is 1.

* * * * *

UNITED STATES PATENT AND TRADEMARK OFFICE
CERTIFICATE OF CORRECTION

PATENT NO. : 4,841,045

DATED : June 20, 1989

INVENTOR(S) : Martin Kuehne

It is certified that error appears in the above-identified patent and that said Letters Patent is hereby corrected as shown below:

In the Specification:

Column 45, line 28, change "3aR, 4R and 3aS, 4R" to read --3aR, 4R and 3aS, 4S--.

Column 45, line 49, change "3aR, 4S and 3aS, 4R" to read --3aR, 4R and 3aS, 4S--.

Column 45, line 64, change "4R title isomer" to read --4S title isomer--.

Column 45, line 66, change "4S" to read --4R--.

Column 46, line 3 change "3aR, 4S" to read --3aR, 4R--.

Column 46, line 8, change "4S" to read --4R--.

Column 46, line 27, change "3aR, 4S" to read --4aR, 4R--.

Column 46, line 27, change "4S" to --4R--.

Column 46, line 30, after "64", change "mL" to -- $\mu$L--.

Column 46, line 44, change "7S, 4S" to --7S, 5R"--.

Column 46, line 49, change "4S" to --4R--.

UNITED STATES PATENT AND TRADEMARK OFFICE
CERTIFICATE OF CORRECTION

PATENT NO. : 4,841,045
DATED : June 20, 1989
INVENTOR(S) : Kuehne

It is certified that error appears in the above-identified patent and that said Letters Patent is hereby corrected as shown below:

Column 47, line 20, after "7S," change "4S" to --5R--.

Column 47, line 24, change "4S" to --5R--.

Column 47, line 40, change "Axial" to --Eqatorial--.

Column 47, line 42, change "4S" to --5R--.

Column 47, lines 64 and 65, delete the phrase, starting on line 3, with ", TLCR$_f$" and ending on line 4 with, "purple)" inclusive.

Column 48, line 5 change "7S, 4S" to --7S, 5R--.

Signed and Sealed this

Tenth Day of July, 1990

Attest:

HARRY F. MANBECK, JR.

*Attesting Officer*   Commissioner of Patents and Trademarks